(12) United States Patent
Libbus et al.

(10) Patent No.: US 11,369,794 B2
(45) Date of Patent: *Jun. 28, 2022

(54) IMPLANTABLE NEURAL STIMULATOR WITH MODE SWITCHING

(71) Applicant: Cardiac Pacemakers, Inc., St. Paul, MN (US)

(72) Inventors: Imad Libbus, St. Paul, MN (US); Andrew P. Kramer, Marine on St. Croix, MN (US); William J. Linder, Golden Valley, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 95 days.

This patent is subject to a terminal disclaimer.

(21) Appl. No.: 16/597,620

(22) Filed: Oct. 9, 2019

(65) Prior Publication Data
US 2020/0038662 A1 Feb. 6, 2020

Related U.S. Application Data

(60) Continuation of application No. 15/342,687, filed on Nov. 3, 2016, now Pat. No. 10,493,280, which is a
(Continued)

(51) Int. Cl.
*A61N 1/36* (2006.01)
*A61N 1/368* (2006.01)
*A61M 5/172* (2006.01)

(52) U.S. Cl.
CPC ....... *A61N 1/36135* (2013.01); *A61M 5/1723* (2013.01); *A61N 1/36053* (2013.01);
(Continued)

(58) Field of Classification Search
CPC ............ A61N 1/36135; A61N 1/36053; A61N 1/36114; A61N 1/36128; A61N 1/3605
See application file for complete search history.

(56) References Cited

U.S. PATENT DOCUMENTS

| 3,421,511 A | 1/1969 | Schwartz et al. |
| 3,650,277 A | 3/1972 | Sjostrand et al. |

(Continued)

FOREIGN PATENT DOCUMENTS

| EP | 0547734 A2 | 6/1993 |
| EP | 1421973 A3 | 5/2004 |

(Continued)

OTHER PUBLICATIONS

"U.S. Appl. No. 11/137,038, Appeal Brief mailed Jan. 18, 2010", 35 pgs.

(Continued)

*Primary Examiner* — Eric D. Bertram
(74) *Attorney, Agent, or Firm* — Schwegman Lundberg & Woessner, P.A.

(57) ABSTRACT

Various aspects of the present subject matter relate to an implantable device. Various device embodiments comprise at least one port to connect to at least one lead with at least electrode, stimulation circuitry connected to the at least one port and adapted to provide at least one neural stimulation therapy to at least one neural stimulation target using the at least one electrode, sensing circuitry connected to the at least one port and adapted to provide a sensed signal, and a controller connected to the stimulation circuitry to provide the at least one neural stimulation therapy and to the sensing circuitry to receive the sensed signal. In response to a triggering event, the controller is adapted to switch between at least two modes. Other aspects and embodiments are provided herein.

20 Claims, 10 Drawing Sheets

Related U.S. Application Data continuation of application No. 14/318,785, filed on Jun. 30, 2014, now Pat. No. 9,486,631, which is a continuation of application No. 13/909,777, filed on Jun. 4, 2013, now Pat. No. 8,768,456, which is a division of application No. 11/137,038, filed on May 25, 2005, now Pat. No. 8,473,049.

(52) U.S. Cl.
CPC ........ *A61N 1/3688* (2013.01); *A61N 1/36114* (2013.01); *A61N 1/36128* (2013.01); *A61N 1/3605* (2013.01)

(56) References Cited

U.S. PATENT DOCUMENTS

| | | | |
|---|---|---|---|
| 4,201,219 A | 5/1980 | Bozal Gonzalez | |
| 4,390,020 A | 6/1983 | Herpers et al. | |
| 4,592,359 A | 6/1986 | Galbraith | |
| 4,699,143 A | 10/1987 | Dufresne et al. | |
| 4,763,646 A | 8/1988 | Lekholm | |
| 4,791,931 A | 12/1988 | Slate | |
| 4,960,129 A | 10/1990 | dePaola et al. | |
| 5,111,815 A | 5/1992 | Mower | |
| 5,199,428 A | 4/1993 | Obel et al. | |
| 5,203,326 A | 4/1993 | Collins | |
| 5,243,980 A | 9/1993 | Mehra | |
| 5,318,592 A | 6/1994 | Schaldach | |
| 5,330,507 A | 7/1994 | Schwartz | |
| 5,334,221 A | 8/1994 | Bardy | |
| 5,356,425 A | 10/1994 | Bardy et al. | |
| 5,411,531 A | 5/1995 | Hill et al. | |
| 5,437,285 A | 8/1995 | Verrier et al. | |
| 5,507,784 A | 4/1996 | Hill et al. | |
| 5,522,854 A | 6/1996 | Ideker et al. | |
| 5,578,061 A | 11/1996 | Stroetmann et al. | |
| 5,658,318 A | 8/1997 | Stroetmann et al. | |
| 5,662,689 A | 9/1997 | Elsberry et al. | |
| 5,690,681 A | 11/1997 | Geddes et al. | |
| 5,700,282 A | 12/1997 | Zabara | |
| 5,731,848 A | 3/1998 | Patel et al. | |
| 5,792,187 A | 8/1998 | Adams | |
| 5,817,131 A | 10/1998 | Elsberry et al. | |
| 5,893,881 A | 4/1999 | Elsberry et al. | |
| 5,916,239 A | 6/1999 | Geddes et al. | |
| 5,928,272 A | 7/1999 | Adkins et al. | |
| 6,006,134 A | 12/1999 | Hill et al. | |
| 6,058,331 A | 5/2000 | King | |
| 6,073,048 A | 6/2000 | Kieval et al. | |
| 6,134,470 A | 10/2000 | Hartlaub | |
| 6,154,675 A | 11/2000 | Juran et al. | |
| 6,178,349 B1 | 1/2001 | Kieval | |
| 6,240,314 B1 | 5/2001 | Plicchi et al. | |
| 6,272,377 B1 | 8/2001 | Sweeney et al. | |
| 6,292,695 B1 | 9/2001 | Webster, Jr. et al. | |
| 6,330,477 B1 | 12/2001 | Casavant | |
| 6,341,236 B1 | 1/2002 | Osorio et al. | |
| 6,371,922 B1 | 4/2002 | Baumann et al. | |
| 6,381,496 B1* | 4/2002 | Meadows | A61N 1/36128 607/59 |
| 6,400,982 B2 | 6/2002 | Sweeney et al. | |
| 6,415,183 B1 | 7/2002 | Scheiner et al. | |
| 6,421,557 B1 | 7/2002 | Meyer | |
| 6,449,507 B1 | 9/2002 | Hill et al. | |
| 6,463,328 B1 | 10/2002 | John | |
| 6,466,822 B1 | 10/2002 | Pless | |
| 6,473,644 B1 | 10/2002 | Terry, Jr. et al. | |
| 6,477,418 B2 | 11/2002 | Plicchi et al. | |
| 6,480,743 B1* | 11/2002 | Kirkpatrick | A61N 1/36135 607/45 |
| 6,487,450 B1 | 11/2002 | Chen et al. | |
| 6,493,585 B2 | 12/2002 | Plicchi et al. | |
| 6,493,586 B1 | 12/2002 | Stahmann et al. | |
| 6,511,500 B1 | 1/2003 | Rahme | |
| 6,522,926 B1 | 2/2003 | Kieval et al. | |
| 6,532,388 B1 | 3/2003 | Hill et al. | |
| 6,542,774 B2 | 4/2003 | Hill et al. | |
| 6,546,288 B1 | 4/2003 | Levine | |
| 6,564,096 B2 | 5/2003 | Mest | |
| 6,611,713 B2 | 8/2003 | Schauerte | |
| 6,622,041 B2 | 9/2003 | Terry, Jr. et al. | |
| 6,628,987 B1 | 9/2003 | Hill et al. | |
| 6,668,191 B1 | 12/2003 | Boveja | |
| 6,690,974 B2 | 2/2004 | Archer et al. | |
| 6,711,442 B1 | 3/2004 | Swerdlow et al. | |
| 6,751,505 B1 | 6/2004 | Van Den Honert et al. | |
| 6,819,953 B2 | 11/2004 | Yonce et al. | |
| 6,889,079 B2 | 5/2005 | Bocek et al. | |
| 6,928,324 B2 | 8/2005 | Park et al. | |
| 6,934,583 B2 | 8/2005 | Weinberg et al. | |
| 6,937,896 B1 | 8/2005 | Kroll | |
| 7,039,466 B1 | 5/2006 | Harrison et al. | |
| 7,089,059 B1* | 8/2006 | Pless | A61B 5/6864 607/45 |
| 7,096,064 B2 | 8/2006 | Deno et al. | |
| 7,123,961 B1 | 10/2006 | Kroll et al. | |
| 7,123,967 B2 | 10/2006 | Weinberg | |
| 7,155,278 B2 | 12/2006 | King et al. | |
| 7,260,431 B2 | 8/2007 | Libbus et al. | |
| 7,277,761 B2 | 10/2007 | Shelchuk | |
| 7,299,086 B2 | 11/2007 | McCabe et al. | |
| 7,414,534 B1 | 8/2008 | Kroll et al. | |
| 7,493,161 B2 | 2/2009 | Libbus et al. | |
| 7,542,800 B2 | 6/2009 | Libbus et al. | |
| 7,570,999 B2 | 8/2009 | Libbus et al. | |
| 7,574,259 B1 | 8/2009 | Pei et al. | |
| 7,587,238 B2 | 9/2009 | Moffitt et al. | |
| 7,657,312 B2 | 2/2010 | Pastore et al. | |
| 7,660,628 B2 | 2/2010 | Libbus et al. | |
| 7,769,450 B2 | 8/2010 | Libbus et al. | |
| 7,840,271 B2 | 11/2010 | Kieval | |
| 7,873,413 B2 | 1/2011 | McCabe et al. | |
| 8,046,069 B2 | 10/2011 | Kramer et al. | |
| 8,131,359 B2 | 3/2012 | Libbus et al. | |
| 8,406,876 B2 | 3/2013 | McCabe et al. | |
| 8,473,049 B2* | 6/2013 | Libbus | A61N 1/36135 607/3 |
| 8,478,397 B2 | 7/2013 | Libbus et al. | |
| 8,504,149 B2 | 8/2013 | Libbus et al. | |
| 8,768,456 B2* | 7/2014 | Libbus | A61N 1/36114 607/3 |
| 8,805,494 B2 | 8/2014 | Libbus et al. | |
| 9,031,650 B2 | 5/2015 | McCabe et al. | |
| 9,211,412 B2 | 12/2015 | McCabe et al. | |
| 9,486,631 B2 | 11/2016 | Libbus et al. | |
| 9,504,836 B2 | 11/2016 | Libbus et al. | |
| 9,962,548 B2 | 5/2018 | McCabe et al. | |
| 10,493,280 B2 | 12/2019 | Libbus et al. | |
| 2001/0020136 A1 | 9/2001 | Sweeney et al. | |
| 2002/0016550 A1 | 2/2002 | Sweeney et al. | |
| 2002/0026221 A1 | 2/2002 | Hill et al. | |
| 2002/0026222 A1 | 2/2002 | Schauerte et al. | |
| 2002/0058877 A1 | 5/2002 | Baumann et al. | |
| 2002/0065473 A1 | 5/2002 | Wang et al. | |
| 2002/0072770 A1 | 6/2002 | Pless | |
| 2002/0077670 A1 | 6/2002 | Archer et al. | |
| 2002/0107553 A1 | 8/2002 | Hill et al. | |
| 2002/0120304 A1 | 8/2002 | Mest | |
| 2002/0123769 A1 | 9/2002 | Panken et al. | |
| 2002/0143369 A1 | 10/2002 | Hill et al. | |
| 2002/0165586 A1 | 11/2002 | Hill et al. | |
| 2002/0169485 A1 | 11/2002 | Pless et al. | |
| 2003/0004549 A1 | 1/2003 | Hill et al. | |
| 2003/0040774 A1 | 2/2003 | Terry, Jr. et al. | |
| 2003/0045909 A1 | 3/2003 | Gross et al. | |
| 2003/0060848 A1 | 3/2003 | Keival et al. | |
| 2003/0060857 A1 | 3/2003 | Perrson et al. | |
| 2003/0060858 A1 | 3/2003 | Kieval et al. | |
| 2003/0074039 A1 | 4/2003 | Puskas | |
| 2003/0078623 A1 | 4/2003 | Weinberg et al. | |
| 2003/0078629 A1 | 4/2003 | Chen | |
| 2003/0100924 A1 | 5/2003 | Foreman et al. | |
| 2003/0144711 A1 | 7/2003 | Pless et al. | |
| 2003/0149450 A1 | 8/2003 | Mayberg | |

(56) References Cited

U.S. PATENT DOCUMENTS

| | | |
|---|---|---|
| 2003/0153953 A1 | 8/2003 | Park et al. |
| 2003/0181951 A1 | 9/2003 | Cates |
| 2003/0212440 A1 | 11/2003 | Boveja |
| 2003/0212445 A1 | 11/2003 | Weinberg |
| 2003/0229380 A1 | 12/2003 | Adams et al. |
| 2004/0002635 A1 | 1/2004 | Hargrove et al. |
| 2004/0024429 A1 | 2/2004 | Daly |
| 2004/0049120 A1 | 3/2004 | Cao et al. |
| 2004/0049235 A1 | 3/2004 | Deno et al. |
| 2004/0082980 A1 | 4/2004 | Mouine et al. |
| 2004/0088009 A1 | 5/2004 | Degroot |
| 2004/0102820 A1 | 5/2004 | Mouine et al. |
| 2004/0133248 A1 | 7/2004 | Frei et al. |
| 2004/0138721 A1 | 7/2004 | Osorio et al. |
| 2004/0138724 A1 | 7/2004 | Sieracki et al. |
| 2004/0162594 A1 | 8/2004 | King |
| 2004/0172074 A1 | 9/2004 | Yoshihito |
| 2004/0172075 A1 | 9/2004 | Shafer et al. |
| 2004/0193231 A1 | 9/2004 | David et al. |
| 2004/0019921 A1 | 10/2004 | Shelchuk |
| 2004/0210261 A1 | 10/2004 | King et al. |
| 2004/0215289 A1 | 10/2004 | Fukui |
| 2005/0010263 A1 | 1/2005 | Schauerte |
| 2005/0027321 A1 | 2/2005 | Ferek-Petric |
| 2005/0060001 A1 | 3/2005 | Singhal et al. |
| 2005/0065553 A1 | 3/2005 | Ben Ezra et al. |
| 2005/0075690 A1 | 4/2005 | Toy et al. |
| 2005/0096705 A1 | 5/2005 | Pastore et al. |
| 2005/0107844 A1 | 5/2005 | Van Den Honert et al. |
| 2005/0115561 A1 | 6/2005 | Stahmann et al. |
| 2005/0143779 A1 | 6/2005 | Libbus |
| 2005/0143785 A1 | 6/2005 | Libbus |
| 2005/0148896 A1 | 7/2005 | Siejko et al. |
| 2005/0149126 A1 | 7/2005 | Libbus |
| 2005/0149127 A1 | 7/2005 | Libbus |
| 2005/0149128 A1 | 7/2005 | Heil, Jr. et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149148 A1 | 7/2005 | King |
| 2005/0149155 A1 | 7/2005 | Scheiner et al. |
| 2005/0149156 A1 | 7/2005 | Libbus et al. |
| 2005/0182389 A1 | 8/2005 | LaPorte et al. |
| 2005/0197674 A1 | 9/2005 | McCabe et al. |
| 2005/0251216 A1 | 11/2005 | Hill et al. |
| 2005/0261741 A1 | 11/2005 | Libbus et al. |
| 2005/0267542 A1 | 12/2005 | David et al. |
| 2006/0004417 A1 | 1/2006 | Rossing et al. |
| 2006/0020297 A1 | 1/2006 | Gerber et al. |
| 2006/0052831 A1 | 3/2006 | Fukui |
| 2006/0079945 A1 | 4/2006 | Libbus |
| 2006/0095080 A1* | 5/2006 | Libbus ............... A61N 1/36114 607/2 |
| 2006/0106429 A1 | 5/2006 | Libbus et al. |
| 2006/0111632 A1 | 5/2006 | Chen |
| 2006/0116737 A1 | 6/2006 | Libbus |
| 2006/0122675 A1 | 6/2006 | Libbus et al. |
| 2006/0167497 A1 | 7/2006 | Armstrong et al. |
| 2006/0206153 A1 | 9/2006 | Libbus et al. |
| 2006/0206154 A1 | 9/2006 | Moffitt et al. |
| 2006/0206158 A1 | 9/2006 | Wu et al. |
| 2006/0206159 A1 | 9/2006 | Moffitt et al. |
| 2006/0217772 A1 | 9/2006 | Libbus et al. |
| 2006/0224188 A1 | 10/2006 | Libbus et al. |
| 2006/0224202 A1 | 10/2006 | Moffitt et al. |
| 2006/0229677 A1 | 10/2006 | Moffitt et al. |
| 2006/0241699 A1 | 10/2006 | Libbus et al. |
| 2006/0241725 A1 | 10/2006 | Libbus |
| 2006/0259083 A1 | 11/2006 | Libbus et al. |
| 2006/0271118 A1 | 11/2006 | Libbus et al. |
| 2007/0021799 A1 | 1/2007 | Kieval et al. |
| 2007/0142864 A1 | 6/2007 | Libbus et al. |
| 2007/0142871 A1 | 6/2007 | Libbus et al. |
| 2008/0004663 A1 | 1/2008 | Jorgenson |
| 2008/0015648 A1 | 1/2008 | Libbus et al. |
| 2008/0021504 A1 | 1/2008 | McCabe et al. |
| 2008/0167693 A1 | 7/2008 | Kieval et al. |
| 2008/0200959 A1 | 8/2008 | Libbus et al. |
| 2009/0018596 A1 | 1/2009 | Kieval |
| 2009/0228060 A1 | 9/2009 | Libbus et al. |
| 2010/0121399 A1 | 5/2010 | McCabe et al. |
| 2011/0015704 A1 | 1/2011 | Ternes et al. |
| 2011/0106199 A1 | 5/2011 | Mccabe et al. |
| 2011/0137360 A1 | 6/2011 | Ternes et al. |
| 2012/0150250 A1 | 6/2012 | Libbus |
| 2013/0116578 A1 | 5/2013 | An et al. |
| 2013/0197594 A1 | 8/2013 | Mccabe et al. |
| 2013/0267893 A1 | 10/2013 | Libbus et al. |
| 2014/0316487 A1 | 10/2014 | Libbus et al. |
| 2015/0238766 A1 | 8/2015 | Mccabe et al. |
| 2016/0082259 A1 | 3/2016 | Mccabe et al. |
| 2017/0050026 A1 | 2/2017 | Libbus et al. |

FOREIGN PATENT DOCUMENTS

| | | |
|---|---|---|
| EP | 1426078 A1 | 6/2004 |
| JP | 2005501617 A | 1/2005 |
| JP | 5015915 B2 | 9/2012 |
| WO | WO-9216257 A1 | 10/1992 |
| WO | WO-03011388 A2 | 2/2003 |
| WO | WO-03018108 A3 | 3/2003 |
| WO | WO-03076008 A1 | 9/2003 |
| WO | WO-03099377 A1 | 12/2003 |
| WO | WO-20030099377 A1 | 12/2003 |
| WO | WO-2004084993 A1 | 10/2004 |
| WO | WO-04110549 A2 | 12/2004 |
| WO | WO-2005042091 A1 | 5/2005 |
| WO | WO-2006055436 A1 | 5/2005 |
| WO | WO-2005063332 A1 | 7/2005 |
| WO | WO-2005113066 A1 | 12/2005 |
| WO | WO-2006044025 A1 | 4/2006 |
| WO | WO-2006107675 A1 | 10/2006 |
| WO | WO-2006121929 A1 | 11/2006 |
| WO | WO-2006127248 A1 | 11/2006 |
| WO | WO-2007078410 A1 | 7/2007 |
| WO | WO-2008063396 A1 | 5/2008 |
| WO | WO-2008144354 A1 | 11/2008 |
| WO | WO-2011008749 A2 | 1/2011 |
| WO | WO-2011088222 A1 | 7/2011 |

OTHER PUBLICATIONS

"U.S. Appl. No. 11/137,038, Appeal Brief filed May 4, 2009", 34 pgs.

"U.S. Appl. No. 11/137,038, Appeal Brief filed Jan. 18, 2010", 35 pgs.

"U.S. Appl. No. 11/137,038, Preliminary Amendment filed Jun. 20, 2006", 11 pgs.

"U.S. Appl. No. 11/137,038, Response filed May 15, 2008 to Non Final Office Action dated Feb. 5, 2008", 13 pgs.

"U.S. Appl. No. 11/137,038, Appeal Decision mailed Dec. 11, 2012", 23 pgs.

"U.S. Appl. No. 11/137,038, Decision on Pre-Appeal Brief Request mailed Feb. 25, 2009", 2 pgs.

"U.S. Appl. No. 11/137,038, Examiner's Answer dated Mar. 31, 2010", 10 pgs.

"U.S. Appl. No. 11/137,038, Final Office Action dated Aug. 14, 2009", 10 pgs.

"U.S. Appl. No. 11/137,038, Final Office Action dated Aug. 29, 2008", FOAR, 10 pgs.

"U.S. Appl. No. 11/137,038, Non-Final Office Action dated Feb. 5, 2008", OARN, 8 pgs.

"U.S. Appl. No. 11/137,038, Notice of Allowance dated Feb. 25, 2013", 9 pgs.

"U.S. Appl. No. 11/137,038, Pre-Appeal Brief request for Review filed Jan. 29, 2009", 5 pgs.

"U.S. Appl. No. 11/137,038, Response filed Dec. 13, 2007 to Restriction Requirement Nov. 15, 2007", 12 pgs.

(56) References Cited

OTHER PUBLICATIONS

"U.S. Appl. No. 11/137,038, Restriction Requirement dated Nov. 15, 2007", 8 pgs.
"U.S. Appl. No. 13/909,777, Non Final Office Action dated Oct. 28, 2013", 8 pgs.
"U.S. Appl. No. 13/909,777, Notice of Allowance dated Feb. 20, 2014", 8 pgs.
"U.S. Appl. No. 13/909,777, Response filed Jan. 28, 2014 to Non Final Office Action dated Oct. 28, 2014", 8 pgs.
"U.S. Appl. No. 13/909,777, Response filed Oct. 10, 2013 to Restriction Requirement dated Sep. 11, 2013", 8 pgs.
"U.S. Appl. No. 13/909,777, Restriction Requirement dated Sep. 11, 2013", 6 pgs.
"U.S. Appl. No. 14/318,785, Examiner Interview Summary dated Jul. 18, 2016", 3 pgs.
"U.S. Appl. No. 14/318,785, Examiner Interview Summary dated Aug. 24, 2015", 3 pgs.
"U.S. Appl. No. 14/318,785, Final Office Action dated May 16, 2016", 10 pgs.
"U.S. Appl. No. 14/318,785, Final Office Action dated Jun. 17, 2015", 8 pgs.
"U.S. Appl. No. 14/318,785, Non Final Office Action dated Dec. 2, 2015", 9 pgs.
"U.S. Appl. No. 14/318,785, Non Final Office Action dated Dec. 22, 2014", 7 pgs.
"U.S. Appl. No. 14/318,785, Notice of Allowance dated Aug. 10, 2016", 8 pgs.
"U.S. Appl. No. 14/318,785, Preliminary Amendment filed Jul. 1, 2014", 8 pgs.
"U.S. Appl. No. 14/318,785, Response filed Mar. 2, 2016 to Non Final Office Action dated Dec. 2, 2015", 11 pgs.
"U.S. Appl. No. 14/318,785, Response filed Mar. 23, 2015 to Non Final Office Action dated Dec. 22, 2014", 10 pgs.
"U.S. Appl. No. 14/318,785, Response filed Jul. 14, 2016 to Final Office Action dated May 16, 2016", 9 pgs.
"U.S. Appl. No. 14/318,785, Response filed Aug. 21, 2015 to Final Office Action dated Jun. 17, 2015", 10 pgs.
"U.S. Appl. No. 14/318,785, Response filed Oct. 28, 2014 to Restriction Requirement dated Aug. 28, 2014", 8 pgs.
"U.S. Appl. No. 14/318,785, Restriction Requirement dated Aug. 28, 2014", 6 pgs.
"U.S. Appl. No. 14/958,413, Notice of Allowance dated Jan. 10, 2018", 9 pgs.
"U.S. Appl. No. 14/958,413, Response filed Dec. 12, 2017 to Final Office Action dated Sep. 12, 2017", 8 pgs.
"U.S. Appl. No. 15/342,687, Advisory Action dated Sep. 4, 2018", 3 pgs.
"U.S. Appl. No. 15/342,687, Final Office Action dated May 15, 2019", 7 pgs.
"U.S. Appl. No. 15/342,687, Final Office Action dated Jun. 26, 2018", 13 pgs.
"U.S. Appl. No. 15/342,687, Non Final Office Action dated Oct. 25, 2018", 10 pgs.
"U.S. Appl. No. 15/342,687, Non Final Office Action dated Dec. 13, 2017", 10 pgs.
"U.S. Appl. No. 15/342,687, Notice of Allowance dated Aug. 1, 2019", 7 pgs.
"U.S. Appl. No. 15/342,687, Preliminary Amendment filed Nov. 9, 2016", 7 pgs.
"U.S. Appl. No. 15/342,687, Response filed Mar. 12, 2018 to Non Final Office Action dated Dec. 13, 2017", 10 pgs.
"U.S. Appl. No. 15/342,687, Response filed Jul. 15, 2019 to Final Office Action dated May 15, 2019", 8 pgs.
"U.S. Appl. No. 15/342,687, Response filed Aug. 27, 2018 to Final Office Action dated Jun. 26, 2018", 9 pgs.
"U.S. Appl. No. 15/342,687, Response filed Sep. 20, 2017 to Restriction Requirement dated Jul. 24, 2017", 7 pgs.
"U.S. Appl. No. 15/342,687, Restriction Requirement dated Jul. 24, 2017", 6 pgs.
"U.S. Appl. No. 15/342,687, Response filed Jan. 25, 2019 to Non Final Office Action dated Oct. 25, 2018", 14 pgs.
"European Application Serial No. 06752374.6, Examination Notification Art. 94(3) dated Jan. 27, 2015", 5 pgs.
"European Application Serial No. 06752374.6; Office Action Filed Mar. 30, 2011", 15.
"European Application Serial No. 06752374.6; Office Action dated Nov. 22, 2010", 4 Pgs.
"International Application Serial No. PCT/US2006/017637, International Search Report and Written Opinion dated Oct. 20, 2006".
"Japanese Application Serial No. 2008-513513, Office Action dated Nov. 14, 2011", with English translation, 9 pgs.
"Japanese Application Serial No. 2008-513513, Response filed Mar. 14, 2012 to Office Action dated Nov. 14, 2011", with English claims, 21 pgs.
Bilgutay, A M, et al., "A new concept in the treatment of hypertension utilizing an implantable electronic device: "Baropacer"", Trans Am Soc Artif Intern Organs., 10, (1964), 387-395.
Li, M., et al., "Vagal nerve stimulation markedly improves long-term survival after chronic heart failure in rats", Circulation, 109(1), (2004), 120-124.
Sigurdsson, A., et al., "The Role of Neurohormonal Activation in Chronic Heart Failure and Postmyocardial Infarction", American Heart Journal, 132(1, Part 2), (Jul. 1996), 229-234.
Vanoli, E., et al., "Vagal Stimulation and Prevention of Sudden Death in Conscious Dogs With a Healed Myocardial Infarction", Circulation Research, 68(5), (May 1991), 1471-1481.
"U.S. Appl. No. 11/482,635, Preliminary Statement Oct. 31, 2006", 2 pgs.
"U.S. Appl. No. 12/469,012, Non Final Office Action dated Sep. 18, 2012", 9 pgs.
"U.S. Appl. No. 12/469,012, Response filed Sep. 4, 2012 to Restriction Requirement dated Aug. 2, 2012", 8 pgs.
"U.S. Appl. No. 12/469,012, Restriction Requirement dated Aug. 2, 2012", 8 pgs.
"U.S. Appl. No. 12/688,575 , Response filed Nov. 1, 2012 to Non Final Office Action dated Aug. 1, 2012", 15 pgs.
"U.S. Appl. No. 12/688,575, Non Final Office Action dated Aug. 1, 2012", 7 pgs.
"U.S. Appl. No. 12/688,575, Notice of Allowance dated Nov. 27, 2012", 9 pgs.
"U.S. Appl. No. 12/688,575, Response to Restriction Requirement dated Mar. 30, 2012", 14 pgs.
"U.S. Appl. No. 12/688,575, Restriction Requirement dated Mar. 30, 2012", 26 pgs.
"U.S. Appl. No. 12/986,762, Notice of Allowance dated Jan. 12, 2015", 8 pgs.
"U.S. Appl. No. 13/397,115, Notice of Publication", 1 pg.
"U.S. Appl. No. 13/798,684, Advisory Action dated Jun. 10, 2015", 3 pgs.
"U.S. Appl. No. 13/798,684, Final Office Action dated Apr. 3, 2015", 10 pgs.
"U.S. Appl. No. 13/798,684, Non Final Office Action dated Sep. 19, 2014", 7 pgs.
"U.S. Appl. No. 13/798,684, Notice of Allowance dated Aug. 10, 2015", 7 pgs.
"U.S. Appl. No. 13/798,684, Response filed Jun. 3, 2015 to Final Office Action dated Apr. 3, 2015", 12 pgs.
"U.S. Appl. No. 13/798,684, Response filed Jun. 25, 2014 to Restriction Requirement dated Apr. 25, 2014", 7 pgs.
"U.S. Appl. No. 13/798,684, Response filed Dec. 18, 2014 to Non Final Office Action dated Sep. 19, 2014", 10 pgs.
"U.S. Appl. No. 13/798,684, Restriction Requirement dated Apr. 25, 2014", 7 pgs.
"U.S. Appl. No. 13/898,069, Advisory Action dated Aug. 10, 2015", 4 pgs.
"U.S. Appl. No. 13/898,069, Final Office Action dated May 20, 2015", 9 pgs.
"U.S. Appl. No. 13/898,069, Response filed Jan. 27, 2015 to Non Final Office Action dated Oct. 8, 2014", 10 pgs.
"U.S. Appl. No. 13/898,069, Response filed Jul. 20, 2015 to Final Office Action dated May 2015", 10 pgs.

(56) References Cited

OTHER PUBLICATIONS

"U.S. Appl. No. 14/013,276, Non Final Office Action dated Apr. 1, 2015", 17 pgs.
"U.S. Appl. No. 14/013,276, Notice of Allowance dated Aug. 28, 2015", 9 pgs.
"U.S. Appl. No. 14/013,276, Response filed Jun. 30, 2015 to Non Final Office Action dated Apr. 1, 2015", 11 pgs.
"U.S. Appl. No. 14/325,634, Non Final Office Action dated Jan. 14, 2015", 13 pgs.
"U.S. Appl. No. 14/325,634, Notice of Allowability dated May 29, 2015", 5 pgs.
"U.S. Appl. No. 14/325,634, Preliminary Amendment filed Jul. 9, 2014", 6 pgs.
"U.S. Appl. No. 14/325,634, Response filed Apr. 9, 2015 to Non Final Office Action dated Jan. 14, 2015", 12 pgs.
"U.S. Appl. No. 14/708,445, Preliminary Amendment filed May 12, 2015", 6 pgs.
"U.S. Appl. No. 14/958,413, Final Office Action dated Sep. 12, 2017", 9 pgs.
"U.S. Appl. No. 14/958,413, Non Final Office Action dated May 24, 2017", 9 pgs.
"U.S. Appl. No. 14/958,413, Preliminary Amendment filed Feb. 9, 2016", 6 pgs.
"U.S. Appl. No. 14/958,413, Response filed Aug. 24, 2017 to Non Final Office Action dated May 24, 2017", 9 pgs.
"U.S. Appl. No. 14/958,413, Response filed Sep. 7, 2016 to Restriction Requirement dated Jul. 8, 2016", 7 pgs.
"U.S. Appl. No. 14/958,413, Restriction Requirement dated Jul. 8, 2016", 9 pgs.
"U.S. Appl. No. 14/958,413, Restriction Requirement dated Dec. 21, 2016", 7 pgs.
"U.S. Appl. No. 14/958,413, Response filed Feb. 16, 2017 to Restriction Required dated Dec. 21, 2016", 8 pgs.
"International Application Serial No. PCT/US2006/042727, International Search Report and Written Opinion dated Apr. 23, 2007", 16 pgs.
"International Application Serial No. PCT/US2011/021154, Search Report dated Mar. 10, 2011", 5 pgs.
"International Application Serial No. PCT/US2011/021154, Written Opinion dated Mar. 10, 2011", 9 pgs.
Andersen, H, et al., "Long-term follow-up of patients from a randomised trial of atrial versus ventricular pacing for sick-sinus syndrome", Lancet, 350(9086), (Oct. 25, 1997), 1210-6.
Benchimol, A, et al., "Cardiac hemodynamics during stimulation of the right atrium, right ventricle, and left ventricle in normal and abnormal hearts", Circulation, 33(6), (Jun. 1966), 933-44.
Bevan, J A, et al., "Postganglionic sympathetic delay in vascular smooth muscle", Journal of Pharmacology & Experimental Therapeutics, 152(2), (May 1966), 221-30.
Bevan, J A, et al., "Sympathetic nerve-free vascular muscle", Journal of Pharmacology & Experimental Therapeutics, 157(1), (Jul. 1967), 117-24.
Bilgutay, A M, et al., "Vagal tuning for the control of supraventricular arrhythmias", Surgical Forum, 16, (1965), 151-3.
Bilgutay, A. M, et al., "Vagal tuning. A new concept in the treatment of supraventricular arrhythmias, angina pectoris, and heart failure", Journal of Thoracic and Cardiovascular Surgery, 56(1), (Jul. 1968), 71-82.
Borst, C, et al., "Optimal frequency of carotid sinus nerve stimulation in treatment of angina pectoris", Cardiovascular Research, 8(5), (Sep. 1974), 674-80.
Braunwald, E, et al., "Carotid sinus nerve stimulation in the treatment of angina pectoris and supraventricular tachycardia", California Medicine, 112(3), (Mar. 1970), 41-50.
Braunwald, E, et al., "Relief of angina pectoris by electrical stimulation of the carotid-sinus nerves", New England Journal of Medicine, 277(24), (Dec. 14, 1967), 1278-83.
Chapleau, M W, et al., "Pulsatile activation of baroreceptors causes central facilitation of baroreflex", American Journal of Physiology, 256(6 Pt 2), (Jun. 1989), H1735-41.

Chapleau, M. W., et al., "Contrasting effects of static and pulsatile pressure on carotid baroreceptor activity in dogs", Circulation, vol. 61, No. 5, (Nov. 1987), 648-658.
Coleridge, J C, et al., "Relationship between pulmonary arterial pressure and impulse activity in pulmonary arterial baroreceptor fibres", Journal of Physiology, 158, (Sep. 1961), 197-205.
Coleridge, J C, et al., "The distribution, connexions and histology of baroreceptors in the pulmonary artery, with some observations on the sensory innervation of the ductus arteriosus", Journal of Physiology, 156, (May 1961), 591-602.
Cooper, Terry B, et al., "Neural effects on sinus rate and atrioventricular conduction produced by electrical stimulation from a transvenous electrode catheter in the canine right pulmonary artery", Circulation Research, vol. 46, No. 1, (Jan. 1980), 48-57.
Courtice, G P, et al., "Effect of frequency and impulse pattern on the non-cholinergic cardiac response to vagal stimulation in the toad, *Bufo marinus*", Journal of the Autonomic Nervous System, 48(3), (Aug. 1994), 267-72.
Dart, JR., C H, et al., "Carotid sinus nerve stimulation treatment of angina refractory to other surgical procedures", Annals of Thoracic Surgery, 11(4), (Apr. 1971), 348-59.
De Landsheere, D, et al., "Effect of spinal cord stimulation on regional myocardial perfusion assessed by positron emission tomography", American Journal of Cardiology, 69(14), (May 1, 1992), 1143-9.
Dunning, A. J., "Electrostimulation of the Carotid Sinus Nerve in Angina Pectoris", University Department of Medicine, Binnengasthuis, Amsterdam; Printed by Royal VanGorcum, Assen, Netherlands, (1971), 1-92.
Epstein, S. E., et al., "Treatment of angina pectoris by electrical stimulation of the carotid-sinus nerves", New England Journal of Medicine, 280(18), (May 1, 1969), 971-978.
Farrehi, C, "Stimulation of the carotid sinus nerve in treatment of angina pectoris", American Heart Journal, 80(6), (Dec. 1970), 759-65.
Feliciano, L, et al., "Vagal nerve stimulation releases vasoactive intestinal peptide which significantly increases coronary artery blood flow", Cardiovascular Research, 40(1), (Oct. 1998), 45-55.
Fromer, M, et al., "Ultrarapid subthreshold stimulation for termination of atrioventricular node reentrant tachycardia", Journal of the American College of Cardiology, 20(4), (Oct. 1992), 879-83.
Grassi, Guido, et al., "Baroreflex and non-baroreflex modulation of vagal cardiac control after myocardial infarction", Am J Cardiol., 84(5), (Sep. 1, 1999), 525-529.
Griffith, Lawrence S.C., et al., "Electrical Stimulation of the Carotid Sinus Nerve in Normotensive and Renal Hypertensive Dogs", Circulation, 28, (Jul.-Dec. 1963), 730.
Henning, R J, et al., "Effects of autonomic nerve stimulation, asynchrony, and load on dP/dtmax and on dP/dtmin", American Journal of Physiology, 260(4 Pt 2), (Apr. 1991), H1290-H1298.
Henning, R J, et al., "Vagal nerve stimulation increases right ventricular contraction and relaxation and heart rate", Cardiovascular Research, 32(5), (Nov. 1996), 846-53.
Henning, R J, et al., "Vagal stimulation attenuates sympathetic enhancement of left ventricular function", American Journal of Physiology, 258(5 Pt 2), (May 1990), H1470-5.
Holmgren, C., et al., "Risk of interference from transcutaneous electrical nerve stimulation on the sensing function of implantable defibrillators", Pacing Clin Electrophysiol., 31(2), (Feb. 2008), 151-8.
Hood JR., W B, et al., "Asynchronous contraction due to late systolic bulging at left ventricular pacing sites", American Journal of Physiology, 217(1), (Jul. 1969), 215-21.
Ishise, H, et al., "Time course of sympathovagal imbalance and left ventricular dysfunction in conscious dogs with heart failure", Journal of Applied Physiology, 84(4), (Apr. 1998), 1234-41.
Jessurun, G A, et al., "Coronary blood flow dynamics during transcutaneous electrical nerve stimulation for stable angina pectoris associated with severe narrowing of one major coronary artery", American Journal of Cardiology, 82(8), erratum appears in Am J Cardiol Feb. 15, 1995;83(4):642, (Oct. 15, 1998), 921-6.

(56) References Cited

OTHER PUBLICATIONS

Kandel, Eric R, et al., "Part VII: Arousal, Emotion, and Behavioral Homeostasis", In: Principles of Neural Science, New York : McGraw-Hill, Health Professions Division, (2000), 966-969.

Karpawich, P P, et al., "Altered cardiac histology following apical right ventricular pacing in patients with congenital atrioventricular block", Pacing Clin Electrophysiol., 22(9), (Sep. 1999), 1372-7.

Leclercq, C, et al., "Hemodynamic importance of preserving the normal sequence of ventricular activation in permanent cardiac pacing", Am Heart J., 129(6), (Jun. 1995), 1133-41.

Levy, M. N., et al., "Effects of Repetitive Bursts of Vagal Activity on Heart Rate", Circulation Research, 30(2), (1972), 186-195.

Mannheimer, C, et al., "Epidural spinal electrical stimulation in severe angina pectoris", British Heart Journal, 59(1), (Jan. 1988), 56-61.

Mannheimer, C, et al., "Transcutaneous electrical nerve stimulation (TENS) in angina pectoris", Pain, 26(3), (Sep. 1986), 291-300.

Mannheimer, C, et al., "Transcutaneous electrical nerve stimulation in severe angina pectoris", European Heart Journal, 3(4), (Aug. 1982), 297-302.

Martin, P., "Time-dependent heart period and contractility responses to successive brief vagal stimuli", Am J Physiol, 239(4), (Oct. 1980), H494-H500.

Mazgalev, T N, et al., "Autonomic modification of the atrioventricular node during atrial fibrillation: role in the slowing of ventricular rate", Circulation, 99(21), (Jun. 1, 1999), 2806-14.

Millar-Craig, M W, et al., "Circadian variation of blood-pressure", Lancet, 1(8068), (Apr. 15, 1978), 795-7.

Minisi, A J, et al., "Regional left ventricular deafferentation increases baroreflex sensitivity following myocardial infarction", Cardiovasc Res., 58(1), (Apr. 1, 2003), 136-41.

Murphy, D F, et al., "Intractable angina pectoris: management with dorsal column stimulation", Medical Journal of Australia, 146(5), (Mar. 2, 1987), 260.

Neistadt, A, et al., "Effects of electrical stimulation of the carotid sinus nerve in reversal of experimentally induced hypertension", Surgery, 61(6), (Jun. 1967), 923-31.

Nolan, J., et al., "Prospective Study of Heart Rate Variability and Mortality in Chronic Heart Failure: Results of the United Kingdom Heart Failure Evaluation and Assessment of Risk Trial (UK-Heart).", Circulation, 98(15), (1998), 1510-1516.

Peters, T K, et al., "Temporal and spatial summation caused by aortic nerve stimulation in rabbits. Effects of stimulation frequencies and amplitudes", Journal of the Autonomic Nervous System, 27(3), (Aug. 1989), 193-205.

Peters, T K, et al., "The principle of electrical carotid sinus nerve stimulation: a nerve pacemaker system for angina pectoris and hypertension therapy", Annals of Biomedical Engineering, 8(4-6), (1980), 445-458.

Philbin, D M, et al., "Inappropriate shocks delivered by an ICD as a result of sensed potentials from a transcutaneous electronic nerve stimulation unit", Pacing & Clinical Electrophysiology, 21(10), (Oct. 1998), 2010-1.

Prakash, P, et al., "Asymmetrical distribution of aortic nerve fibers in the pig", Anat Rec., 158(1), (May 1967), 51-7.

Rosenqvist, M, et al., "The effect of ventricular activation sequence on cardiac performance during pacing", Pacing and Electrophysiology, 19(9), (1996), 1279-1286.

Rushmer, Robert F, "Chapter 5—Systemic Arterial Pressure", In: Cardiovascular dynamics, Philadelphia : Saunders, (1976), 176-216.

Schauerte, P, et al., "Catheter stimulation of cardiac parasympathetic nerves in humans: a novel approach to the cardiac autonomic nervous system", Circulation, 104(20), (Nov. 13, 2001), 2430-5.

Schauerte, P, et al., "Ventricular rate control during atrial fibrillation by cardiac parasympathetic nerve stimulation: a transvenous approach", J Am Coll Cardiol., 34(7), (Dec. 1999), 2043-50.

Schauerte, P. N, et al., "Transvenous parasympathetic cardiac nerve stimulation: an approach for stable sinus rate control", Journal of Cardiovascular Electrophysiology, 10(11), (Nov. 1999), 1517-1524.

Schauerte, P., et al., "Transvenous parasympathetic nerve stimulation in the inferior vena cava and atrioventricular conduction", Journal of Cardiovascular Electrophysiology, 11(1), (Jan. 2000), 1 pg.

Scherlag, M A., et al., "Endovascular Neural Stimulation Via a Novel Basket Electrode Catheter: Comparison of Electrode Configurations", Journal of Interventional Cardiac Electrophysiology, 4(1), (Apr. 2000), 219-224.

Takahashi, N, et al., "Vagal modulation of ventricular tachyarrhythmias induced by left ansae subclaviae stimulation in rabbits", Japanese Heart Journal, 39(4), (Jul. 1998), 503-11.

Tse, H F, et al., "Long-term effect of right ventricular pacing on myocardial perfusion and function", J Am Coll Cardiol., 29(4), (Mar. 15, 1997), 744-9.

Veerman, D P, et al., "Circadian profile of systemic hemodynamics", Hypertension, 26(1), (Jul. 1995), 55-9.

Verity, M A, et al., "Plurivesicular nerve endings in the pulmonary artery", Nature, 211(48), (Jul. 30, 1966), 537-8.

Verity, M, et al., "Pulmonary artery innervation: a morphopharmacologic correlation", Proceedings of the Western Pharmacology Society, 8, (1965), 57-9.

Wallick, D W, et al., "Selective AV nodal vagal stimulation improves hemodynamics during acute atrial fibrillation in dogs", American Journal of Physiology—Heart & Circulatory Physiology, 281(4), (Oct. 2001), H1490-7.

Waninger, M S, et al., "Electrophysiological control of ventricular rate during atrial fibrillation", Pacing & Clinical Electrophysiology, 23(8), (Aug. 2000), 1239-44.

Wiggers, C J, et al., "The muscular reactions of the mammalian ventricles to artificial surface stimuli", American Journal of Physiology, (1925), 346-378.

Zhang, Y, et al., "Optimal ventricular rate slowing during atrial fibrillation by feedback AV nodal-selective vagal stimulation", American Journal of Physiology—Heart & Circulatory Physiology, 282(3), (Mar. 2002), H1102-10.

Zhou, X, et al., "Prevention of high incidence of neurally mediated ventricular arrhythmias by afferent nerve stimulation in dogs", Circulation, 101(7), (Feb. 22, 2000), 819-24.

* cited by examiner

IMPLANTABLE NEURAL STIMULATOR WITH MODE SWITCHING

CLAIM OF PRIORITY

This application is a continuation of U.S. application Ser. No. 15/342,687, filed Nov. 3, 2016, now issued as U.S. Pat. No. 10,493,280, which continuation of U.S. application Ser. No. 14/318,785, filed Jun. 30, 2014, now issued as U.S. Pat. No. 9,486,631, which continuation of U.S. application Ser. No. 13/909,777, filed Jun. 4, 2013, now issued as U.S. Pat. No. 8,768,456, which is a division of U.S. application Ser. No. 11/137,038, filed May 25, 2005, now issued as U.S. Pat. No. 8,473,049, each of which is hereby incorporated by reference in its entirety.

TECHNICAL FIELD

This application relates generally to medical devices and, more particularly, to implantable devices capable of providing neural stimulation.

BACKGROUND

Neural stimulation has been the subject of a number of studies and has been proposed for several therapies. Direct electrical stimulation of parasympathetic nerves can activate the baroreflex, inducing a reduction of sympathetic nerve activity and reducing blood pressure by decreasing vascular resistance. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

SUMMARY

Various aspects of the present subject matter relate to an implantable device. Various device embodiments comprise at least one port to connect to at least one lead with at least electrode, stimulation circuitry, sensing circuitry and a controller. The stimulation circuitry is connected to the at least one port and adapted to provide at least one neural stimulation therapy to at least one neural stimulation target using the at least one electrode. The sensing circuitry is connected to the at least one port and adapted to provide a sensed signal. The controller is connected to the stimulation circuitry to provide the at least one neural stimulation therapy and to the sensing circuitry. In response to a triggering event, the controller is adapted to switch between at least two modes.

In response to a triggering event, the controller of various device embodiments is adapted to switch between at least two modes selected from the group consisting of a stimulation and sensing mode, a stimulation mode, and a sensing mode. In the stimulation and sensing mode, the neural stimulation therapy is provided using a sensed signal. In the stimulation mode, the neural stimulation therapy is provided without using the sensed signal. In the sensing mode, the neural stimulation therapy is not provided to the neural stimulation target.

In response to a triggering event, the controller of various device embodiments is adapted to switch between at least two modes to switch neural stimulation targets. In response to a triggering event, the controller of various device embodiments is adapted to switch between at least two modes to switch sensing sites from which to provide the sensed signal, to switch sensed parameters used to provide the sensed signal, or to switch both sensing sites and sensed parameters.

Various system embodiments comprise at least one port to connect to at least one lead with at least electrode, at least one stimulation circuit connected to the at least one port and adapted to provide at least one neural stimulation therapy to at least one neural stimulation target and to provide a cardiac rhythm management (CRM) therapy using the at least one electrode, at least one sensing circuit connected to the at least one port and adapted to provide a sensed signal, and a controller connected to the at least one stimulation circuit to provide the at least one neural stimulation therapy and the CRM therapy and to the sensing circuitry. In response to a triggering event the controller is adapted to switch between at least two modes selected from the group consisting of a neural stimulation therapy mode, a CRM therapy mode, and a neural stimulation and CRM therapy mode. In the neural stimulation therapy mode, the neural stimulation therapy is provided to the neural target. In the CRM therapy mode, the CRM therapy is provided. In the neural stimulation and CRM therapy mode, the neural stimulation therapy is provided to the neural stimulation target and the CRM therapy is provided.

In various device embodiments, the controller is adapted to operate the device in at least two modes and to switch modes in response to a triggering event. The at least two modes are provided in at least one set of modes selected from the group consisting of a set of operation modes, a set of stimulation site modes and a set of feedback modes. In some embodiments, the group further consists of a set of therapy modes such that the device is able to switch between or among two or more therapy modes. Examples of operation modes includes a mode to provide neural stimulation and sensing, a mode to provide neural stimulation without sensing, and a mode to provide sensing without neural stimulation. Examples of stimulation site modes includes a mode to provide neural stimulation to a first neural stimulation site(s) or target(s) and a mode to provide neural stimulation to a second neural stimulation site(s) or target(s). Examples of feedback modes includes a mode to sense from a first site and a mode to sense from a second site, and also includes a mode to sense a first parameter and a mode to sense a second parameter. Examples of therapy modes include neural stimulation therapy, CRM therapy, drug therapy, and combinations thereof.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
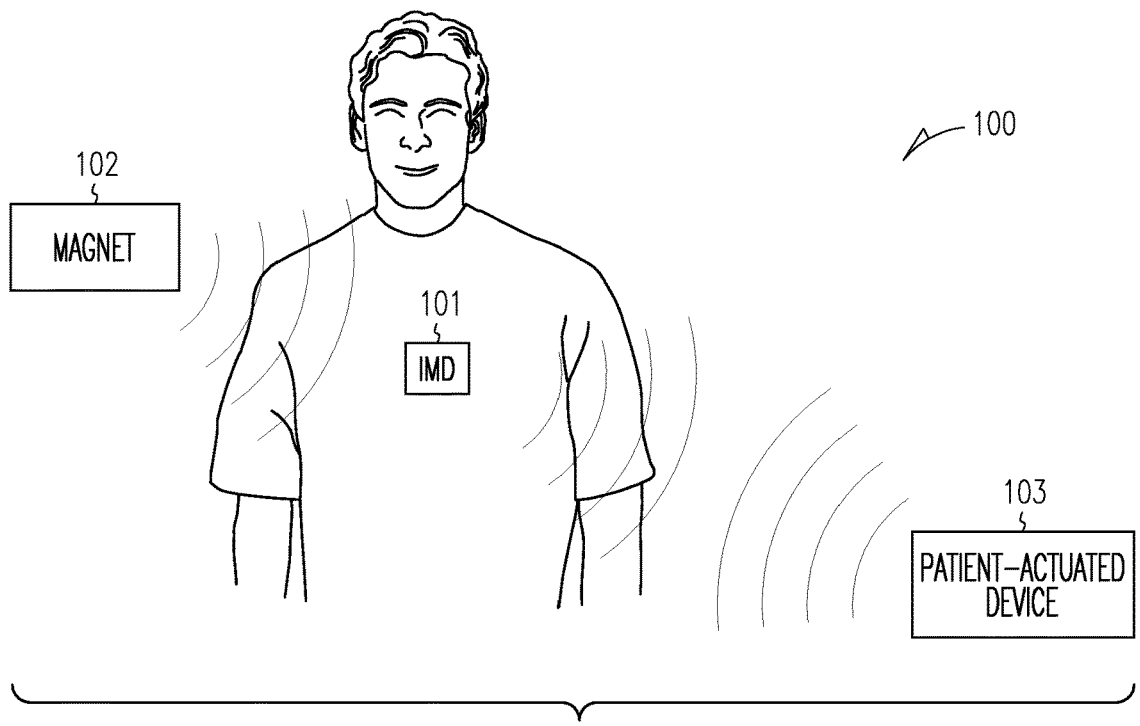
FIG. 1 illustrates an embodiment of a system with an implantable medical device (IMD).

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to an implantable device that provides neural stimulation. In various embodiments, the device also provides neural sensing. In addition to neural stimulation therapy, various device embodiments are adapted to provide cardiac rhythm management (CRM) therapy such as pacing, defibrillation, cardiac resynchronization therapy (CRT) or a combination of pacing, defibrillation and CRT. In addition to neural stimulation therapy, various device embodiments are adapted to provide drug therapy. Some embodiments are adapted to provide various combinations of neural stimulation therapy, CRM therapy and drug therapy. Some therapeutic mode switches include switching among CRM therapies to treat various conditions such as atrial fibrillation, bradycardia and ventricular tachycardia.

The device operates using at least two modes, and has the capability to switch between different modes in response to a triggering event. A variety of mode types are capable of being switched. Some embodiments change modes within a set of operation modes. For example, the device detects the presence of an unacceptably high level of electrical interference, and switches to a "stimulate only" mode in which neural sensing is disabled, or to a "sense only" mode in which neural stimulation is disabled. Some embodiments change modes to change the site or sites of neural stimulation. For example, the device reverts to an alternate lead or electrode in response to a detected electrode failure. Some embodiments change modes within a set of feedback modes to change sensing sites and/or sensed parameters. Some embodiments are adapted to switch between or among various combinations of neural stimulation therapy, CRM therapy, and drug therapy.

The triggering event to switch modes can be automatic or patient-actuated. Examples of patient-actuated triggers include a magnet placed proximate to the implantable device and an external controller unit. For example, some device embodiments switch to a "sense only' mode in response to an external magnet, providing an emergency shut-off mechanism. Some device embodiments toggle between two or among three or more different modes of operation in response to an external magnet. Some device embodiments allow the user (e.g. patient) to select the mode of operation with an external controller unit. An example of an automatic triggering event includes detected noise, where the device detects the presence of an unacceptably high level of electrical interference, and switches to a "stimulate only" mode in which neural sensing is disabled, or to a "sense only" mode in which neural stimulation is disabled.

FIG. 1 illustrates an embodiment of a system 100 with an implantable medical device (IMD) 101. The IMD is adapted to switch modes in response to a triggering event. According to various embodiments, the triggering event is an automatic event, a patient-actuated event, or a combination of an automatic and patient-actuated events. Examples of automatic triggering events include a detected device change such as a detected electrode failure, an End Of Life (EOL) determination for a battery to power the device, a detected lead failure, an environmental change like a detected electrical interference that is capable of interfering with the sensed signal or the application of another therapy capable of interfering with the sensed signal. Automatic triggering events can also include a detected physiologic change such as a detected change in heart rate, a detected arrhythmia, a detected change in a respiratory rate, a detected change in neural traffic, a detected change in blood pressure, and a detected change in activity. Automatic triggering events can also be based on a timer or clock, such as a device with a controller and timer adapted to follow a circadian rhythm when switching modes. Examples of patient-actuated triggers include an external magnet 102 used to actuate a switch (e.g. reed switch) in the implantable device to switch modes, and a patient-actuated external programmer 103 that enables the patient to selectively choose the mode to which the device should switch.

FIG. 1 also illustrates the IMD 101 communicating with an external device 103 such as a patient-actuated device capable of being used to change modes in the IMD 101. A programmer, capable of providing all programming functions, including mode switching, can also be used to communicate with the IMD. The patient-actuated device can be a stand-alone device designed to only provide the desired mode switching capabilities, or can be integrated into other devices. An example of a patient-actuated device includes a personal digital assistant or other electronic device such as would be used in an advanced patient management (APM) system, which can organize and perform calculations based on recorded data, and later provide the data to a programmer.

Figure 2:
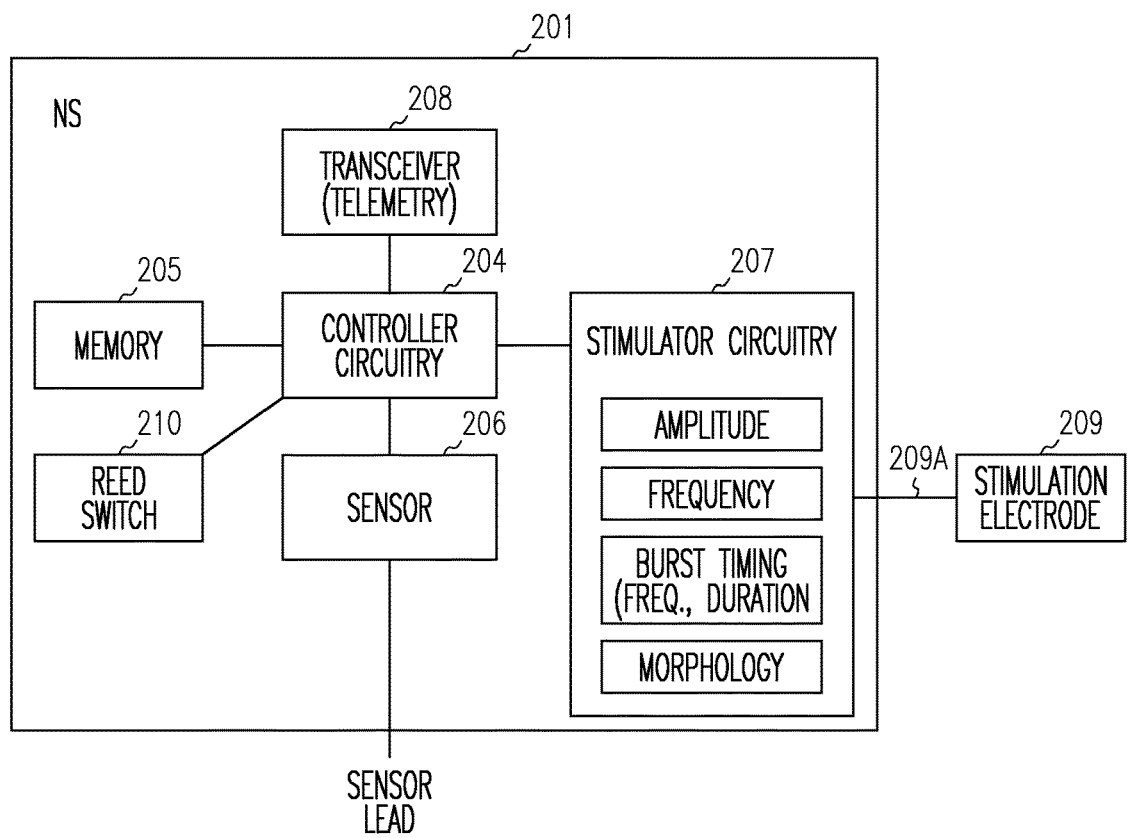
FIG. 2 illustrates an embodiment of an implantable neural stimulator (NS) device such as can be incorporated as the IMD in the system of FIG. 1.

FIG. 2 illustrates an embodiment of an implantable neural stimulator (NS) device 201 such as can be incorporated as the IMD 101 in the system 100 of FIG. 1. The illustrated neural stimulator 201 includes controller circuitry 204 connected to a memory 205, a sensor 206, neural stimulation circuitry 207, and a transceiver 208. An electrode 209 is connected to the stimulator circuitry 207 via a port 209A. The memory includes instructions or algorithms operated on by the controller and further includes parameters for use in the algorithms to provide the desired neural stimulation therapy. These instructions and parameters cooperate to operate the device in a mode. The device can be operated in different modes by operating on different instructions and/or parameters. Some embodiments use the sensor, such as a neural sensor or other physiologic sensor like a heart rate sensor, to provide feedback for the neural stimulation. The stimulator circuitry is adapted to adjust parameters of the neural stimulation signal transmitted to the electrode. According to various embodiments, one or more of the amplitude, the frequency, the morphology and the burst timing (frequency and duration of bursts) are capable of being adjusted. A magnetic-actuated switch 210, such as a reed switch, is connected to the controller for use to receive a user-provided trigger (e.g. flux from the external magnet) to switch modes. Modes can be switched via communications received through the transceiver 208 from the external device or can be automatically switched, such as if mode changes are based on a clock or other feedback. Historical data for mode switching events can be saved in memory 205. The external device can access the memory to display the data regarding the switching events, or can otherwise process the data for a variety of purposes.

Figure 3:
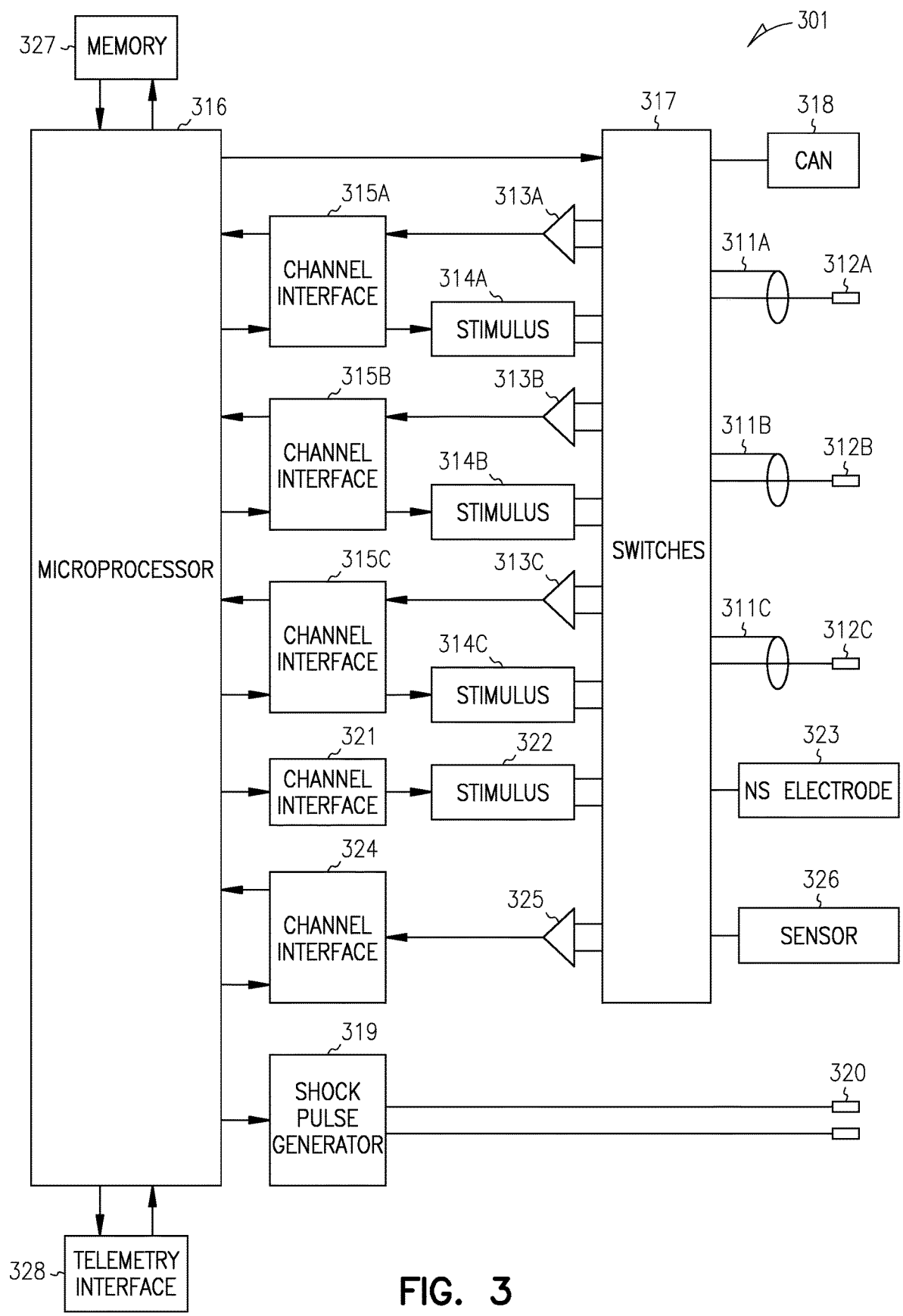
FIG. 3 illustrates a system diagram of an implantable medical device embodiment configured for multi-site stimulation and sensing.

FIG. 3 illustrates a system diagram of an implantable medical device embodiment configured for multi-site stimulation and sensing. This diagram provides another example of an IMD 301 capable of performing a number of neural stimulation and CRM therapies. Pacing, as used in the discussion of this figure, relates to electrical stimulation. In various embodiments, the stimulation for a given channel includes stimulation to capture myocardia, neural stimulation or both pacing and neural stimulation. Three examples of sensing and pacing channels are designated "A" through "C", and such channel can be used to stimulate a right atrium, a right ventricle and a left ventricle, for example. The illustrated channels comprise bipolar leads with ring electrodes 311A-C and tip electrodes 312A-C, sensing amplifiers 313A-C, pulse generators 314A-C, and channel interfaces 315A-C. Each of these channels includes a stimulation channel extending between the pulse generator the electrode and a sensing channel extending between the sense amplifier and the electrode. The channel interfaces 315A-C communicate bidirectionally with microprocessor 316, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry 313A-C detects a chamber sense, either an atrial sense or ventricular sense, when an electrogram signal (i.e., a voltage sensed by an electrode representing cardiac electrical activity) generated by a particular channel exceeds a specified detection threshold. Algorithms, including a number of adjustable parameters, used in particular modes can employ such senses to trigger or inhibit stimulation, and the intrinsic atrial and/or ventricular rates can be detected by measuring the time intervals between atrial and ventricular senses, respectively.

The switching network 317 is used to switch the electrodes to the input of a sense amplifier in order to detect intrinsic cardiac activity and to the output of a pulse generator in order to deliver stimulation. The switching network also enables the device to sense or stimulate either in a bipolar mode using both the ring and tip electrodes of a lead or in a unipolar mode using only one of the electrodes of the lead with the device housing or can 318 serving as a ground electrode or another electrode on another lead serving as the ground electrode. A shock pulse generator 319 is also interfaced to the controller for delivering a defibrillation shock via a pair of shock electrodes 320 to the atria or ventricles upon detection of a shockable tachyarrhythmia. Channel interface 321 and neural stimulation pulse generator 322 provide a connection between the microprocessor and the switch to deliver neural stimulation using the neural stimulation electrode 323. Channel interface 324 and sense amplifier 325 provide a connection between the microprocessor and the switch to receive a sensed signal from a sensor 326 for use to provide feedback for therapies such as a neural stimulation therapy.

The controller or microprocessor controls the overall operation of the device in accordance with programmed instructions and a number of adjustable parameters stored in memory 327, including controlling the delivery of stimulation via the channels, interpreting sense signals received from the sensing channels, and implementing timers for defining escape intervals and sensory refractory periods. The controller is capable of operating the device in a number of programmed stimulation modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited stimulation modes utilize escape intervals to control pacing in accordance with sensed intrinsic activity such that a stimulation pulse is delivered to a heart chamber during a cardiac cycle only after expiration of a defined escape interval during which no intrinsic beat by the chamber is detected. Escape intervals for ventricular stimulation can be restarted by ventricular or atrial events, the latter allowing the pacing to track intrinsic atrial beats. A telemetry interface 328 is also provided which enables the controller to communicate with an external programmer or remote monitor.

Figure 4:
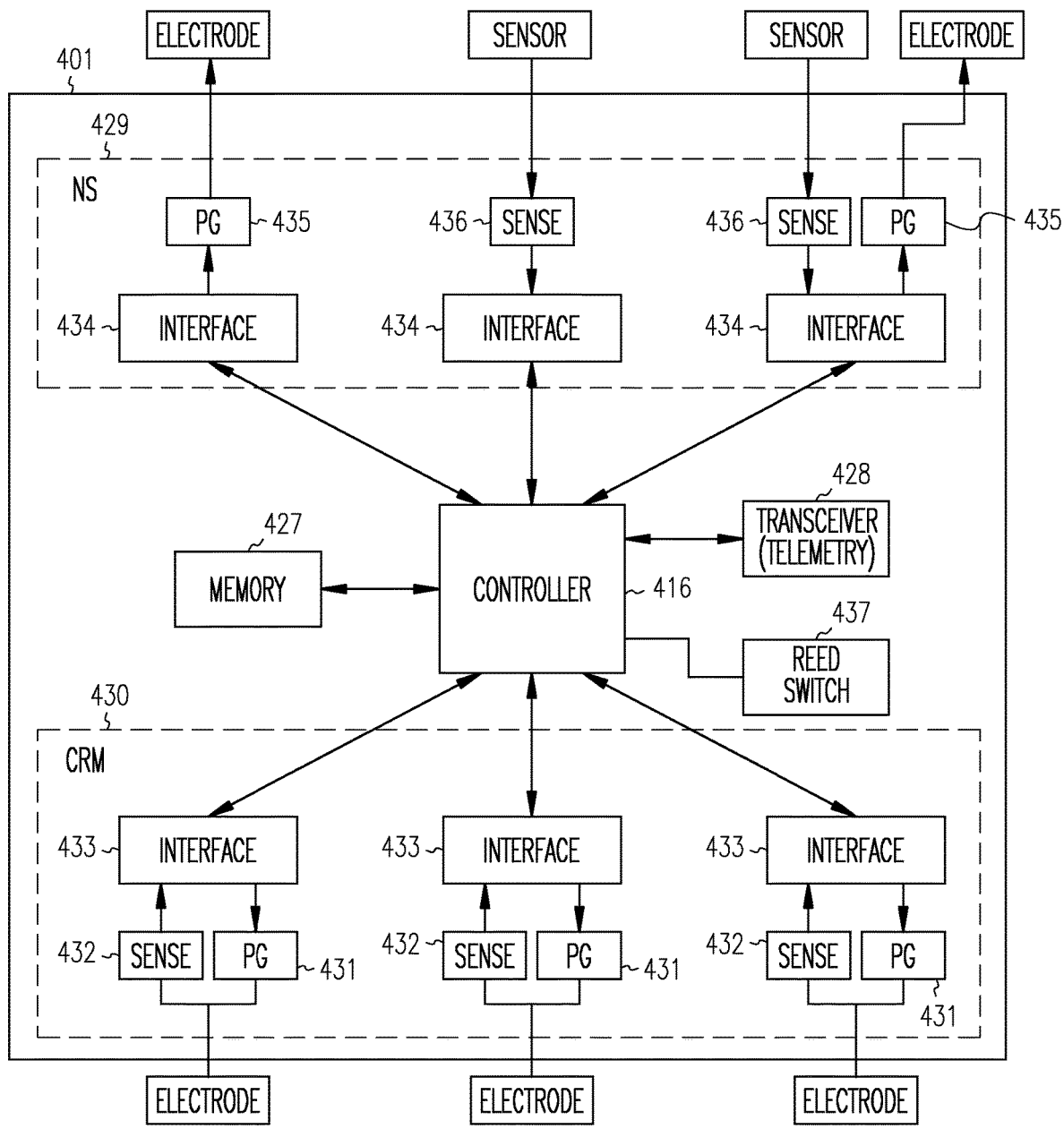
FIG. 4 illustrates an embodiment of an implantable medical device (IMD) such as shown in FIG. 1 having a neural stimulation (NS) component and cardiac rhythm management (CRM) component.

FIG. 4 illustrates an embodiment of an implantable medical device (IMD) 401 such as shown at 101 in FIG. 1 having a neural stimulation (NS) component 429 and cardiac rhythm management (CRM) component 430. The illustrated device 401 includes a controller 416 and a memory 427.

According to various embodiments, the controller includes hardware, software, or a combination of hardware and software to perform the neural stimulation and CRM functions. For example, the programmed therapy applications, including various mode in which the device can operate, discussed in this disclosure are capable of being stored as computer-readable instructions embodied in memory and executed by a processor. According to various embodiments, the controller includes a processor to execute instructions embedded in memory to perform the neural stimulation and CRM functions. The illustrated device 401 further includes a transceiver 428 and associated circuitry for use to communicate with a programmer or another external or internal device. Various embodiments include a telemetry coil.

The CRM therapy section 430 includes components, under the control of the controller, to stimulate a heart and/or sense cardiac signals using one or more electrodes. The CRM therapy section includes a pulse generator 431 for use to provide an electrical signal through an electrode to stimulate a heart, and further includes sense circuitry 432 to detect and process sensed cardiac signals. An interface 433 is generally illustrated for use to communicate between the controller 416 and the pulse generator 431 and sense circuitry 432. Three electrodes are illustrated as an example for use to provide CRM therapy. Ports in the device provides signal channels from the device to the electrodes. The present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 429 includes components, under the control of the controller, to stimulate a neural stimulation target and/or sense autonomic nervous system (ANS) parameters associated with nerve activity or surrogates of ANS parameters such as blood pressure and respiration. Three interfaces 434 are illustrated for use to provide ANS therapy. However, the present subject matter is not limited to a particular number interfaces, or to any particular stimulating or sensing functions. Pulse generators 435 are used to provide electrical pulses through a port to an electrode for use to stimulate a neural stimulation site. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 436 are used to detect and process signals from a sensor, such as a sensor of nerve activity, blood pressure, respiration, and the like. The interfaces 434 are generally illustrated for use to communicate between the controller 416 and the pulse generator 435 and sense circuitry 436. Each interface, for example, may be used to control a separate lead. Various embodiments of the NS therapy section only include a pulse generator to stimulate a neural stimulation target.

According to various embodiments, the lead(s) and the electrode(s) on the leads are physically arranged with respect to the heart in a fashion that enables the electrodes to properly transmit pulses and sense signals from the heart, and with respect to neural targets to stimulate, and in some embodiments sense neural traffic from, the neural targets. Examples of neural targets include both efferent and afferent pathways, such as baroreceptors, nerve trunks and branches such as the vagus nerve, and cardiac fat pads, to provide a desired neural stimulation therapy. As there may be a number of leads and a number of electrodes per lead, the configuration can be programmed to use a particular electrode or electrodes.

The leads of the device include one or more leads to provide CRM therapy, such as atrial pacing, right and/or left ventricular pacing, and/or defibrillation. The device also contains at least one neural stimulation lead which is placed in an appropriate location. Some embodiments perform neural stimulation and CRM therapy using the same lead. Examples of neural stimulation leads include: an expandable stimulation lead placed in the pulmonary artery in proximity of a high concentration of baroreceptors; an intravascularly-fed lead placed proximate to a cardiac fat pad to transvascularly stimulate the fat pad; an epicardial lead with an electrode placed in or proximate to the fat pad; a cuff electrode placed around the aortic, carotid, or vagus nerve; and an intravascularly-fed lead placed to transvascularly stimulate the aortic, carotid or vagus nerve. Other lead placements to stimulate other neural targets may be used.

The controller controls delivery of the electrical pulses, and is adapted to operate the device in a number of different modes. For example various embodiments switch between modes selected from the group consisting of a set of operation modes, a set of stimulation site modes and a set of feedback modes. In some embodiments, the group further consists of a set of therapy modes such that the device is able to switch between or among two or more therapy modes. Examples of operation modes includes a mode to provide neural stimulation and sensing, a mode to provide neural stimulation without sensing, and a mode to provide sensing without neural stimulation. Examples of stimulation site modes includes a mode to provide neural stimulation to a first neural stimulation site(s) or target(s) and a mode to provide neural stimulation to a second neural stimulation site(s) or target(s). Examples of feedback modes includes a mode to sense from a first site and a mode to sense from a second site, and also includes a mode to sense a first parameter and a mode to sense a second parameter. Examples of therapy modes include neural stimulation therapy, CRM therapy, drug therapy, and combinations thereof. In addition, various embodiments are also able to switch between various CRM therapy modes, such as atrial pacing (AOO, AAI), ventricular pacing (VVI, VOO), and or dual chamber pacing (DDI, DDD, VDD), for example. Additionally, changing modes includes changing parameters for a particular pacing mode, such as base rate, upper rate, AV interval, ventricular refractory and ventricular blanking in a DDD pacing mode.

The illustrated device 401 in FIG. 4 includes a switch 437, such as a reed switch, adapted to be actuated by magnetic flux from an external magnet positioned proximate to the device 401. The controller and switch are adapted to switch modes when magnetic flux actuates the switch. In various embodiments, a patient actuated programmer communicates with the controller through the transceiver to change modes. In various embodiments, the controller automatically changes the modes using, for example, a feedback signal or a timer. Historical data for mode switching events can be saved in memory 427. The external device can access the memory to display the data regarding the switching events, or can otherwise process the data for a variety of purposes.

Figure 5:
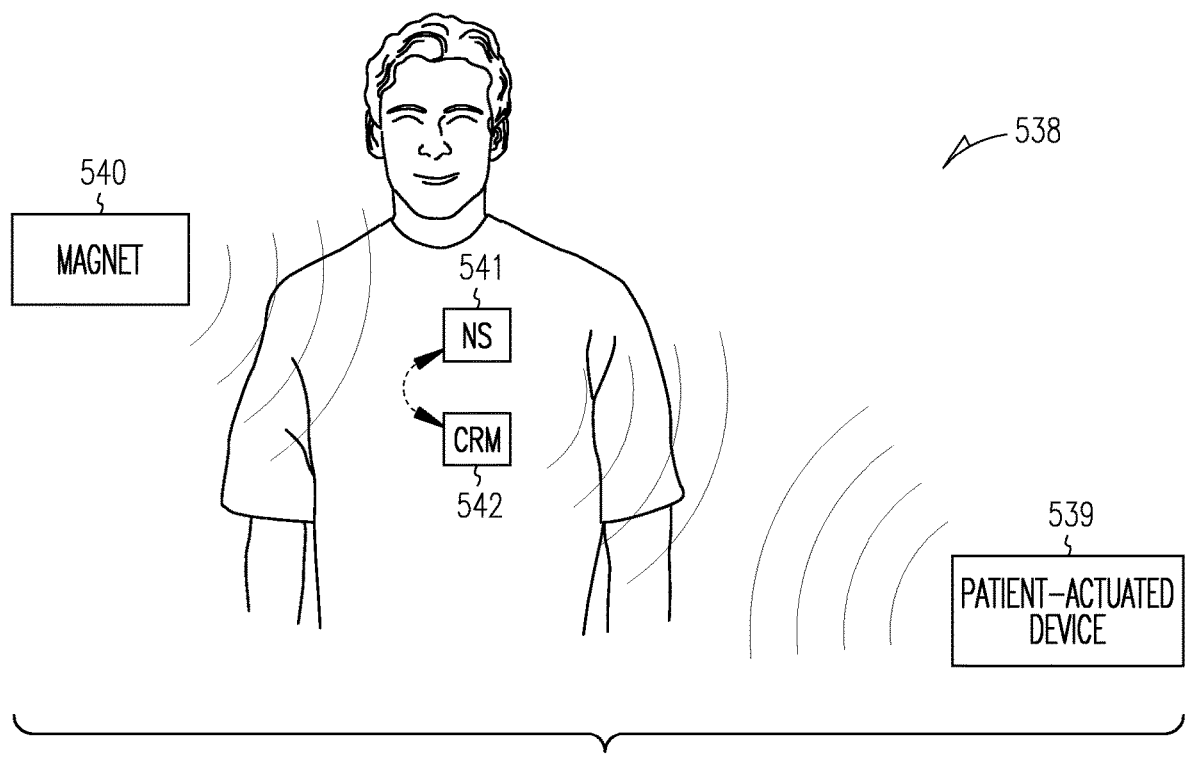
FIG. 5 illustrates a system including a patient-actuated external device, a magnet, an implantable neural stimulator (NS) device and an implantable cardiac rhythm management (CRM) device, according to various embodiments of the present subject matter.

FIG. 5 illustrates a system 538 including a patient-actuated external device 539, a magnet 540, an implantable neural stimulator (NS) device 541 and an implantable cardiac rhythm management (CRM) device 542, according to various embodiments of the present subject matter. Various aspects involve a method for communicating between an NS device and a CRM device or other cardiac stimulator. This communication allows one of the devices 541 or 542 to deliver more appropriate therapy (i.e. more appropriate NS therapy or CRM therapy) based on data and/or communication signals received from the other device. Some embodiments provide on-demand communications. The illustrated NS device and the CRM device are capable of wirelessly communicating with each other, and the programmer is capable of wirelessly communicating with at least one of the NS and the CRM devices. For example, various embodiments use telemetry coils to wirelessly communicate data and instructions to each other. In other embodiments, communication of data and/or energy is by ultrasonic means. In some embodiments, a lead provides a hardwired communication path between the two devices.

Figure 6:
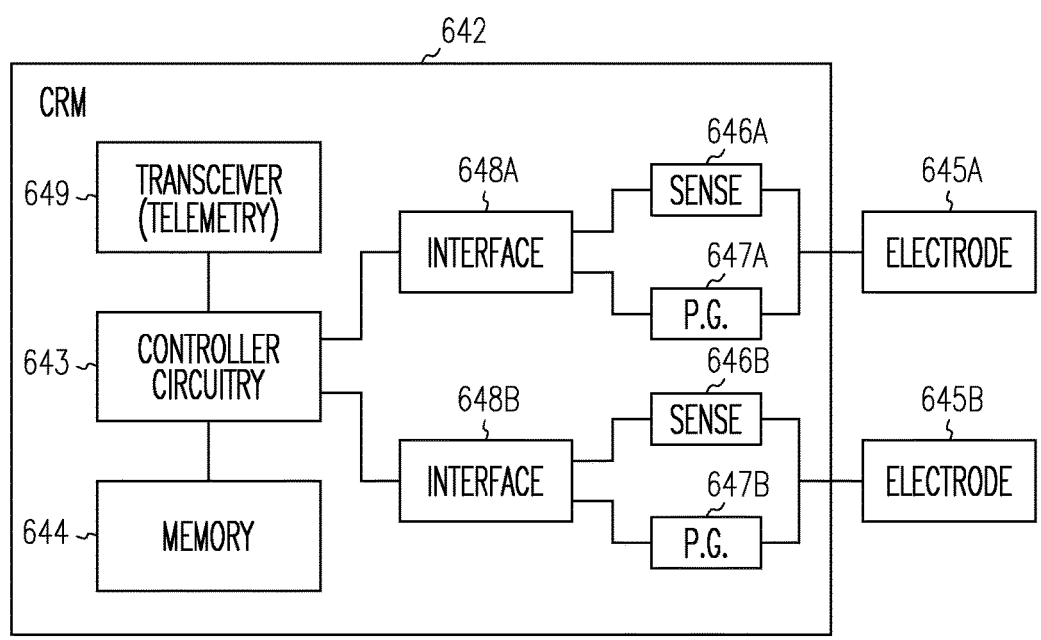
FIG. 6 illustrates an embodiment of CRM device, such as can be used in the system of FIG. 5.

FIG. 6 illustrates an embodiment of CRM device 642, such as can be used at 542 in the system of FIG. 5. The illustrated device 642 includes a controller 643 connected to a memory 644. The figure further illustrates electrodes 645A and 645B connected to the device. According to the illustration, the electrodes 645A and 645B are connected to sense modules 646A and 646B to sense electrical signal at the electrode, and pulse generators 647A and 647B to generate stimulation signals to the electrodes. The controller 643 is connected to the sense modules 646A and 646B and the pulse generator modules 647A and 647B via interfaces 648A and 648B.

The memory includes data and instructions. The controller is adapted to access and operate the instructions to perform various functions within the device, including programmed CRM therapies. The memory 644 includes a plurality of parameters that are used to control the delivery of the therapy using a number of modes. A transceiver 649 is connected to the controller 643. The CRM device is capable of wireless communicating with an external device, for example, using the transceiver 649. For example, various embodiments use telemetry coils to wirelessly communicate data and instructions. In other embodiments, communication of data and/or energy is by ultrasonic means.

Figure 7:
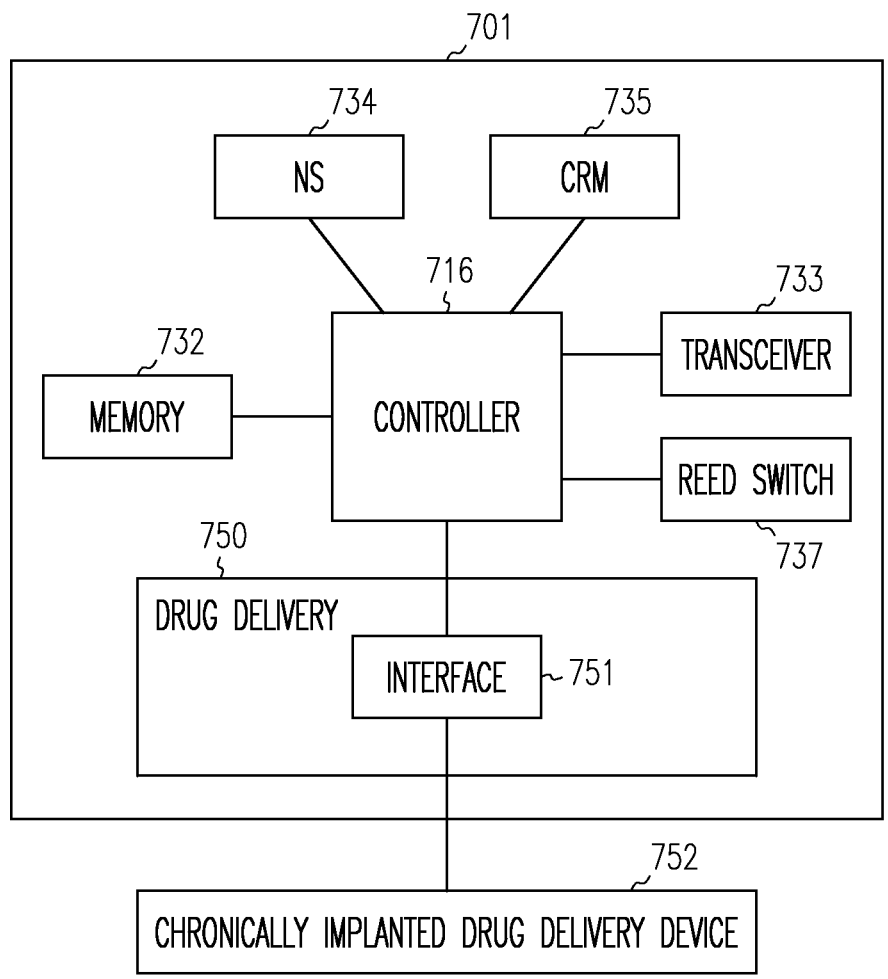
FIG. 7 illustrates an implantable medical device (IMD) such as shown in FIG. 1 having a neural stimulation (NS) component, a cardiac rhythm management (CRM) component, and a drug delivery component, according to various embodiments of the present subject matter.

FIG. 7 illustrates an implantable medical device (IMD) 701 such as shown at 101 in FIG. 1 having a neural stimulation (NS) component 734, a cardiac rhythm management (CRM) component 735, and a drug delivery component 750, according to various embodiments of the present subject matter. Examples of a NS component 734 and a CRM component 735 are illustrated in FIG. 4 at 429 and 430, respectively. The illustrated IMD 701 further includes a controller 716 connected to the therapy components 734, 735 and 750 to control the delivery of the therapies, and also includes a memory 732 to store instructions and data, a transceiver 733, and a magnetic-actuated switch, such as a reed switch 737. The drug delivery component 750 includes an interface 751 to provide an operable connection between the controller 716 and a chronically-implanted drug delivery device 752.

The device is capable of operating in different modes, and switching between or among two or more modes in response to a triggering event. The triggering event can be automatic. Examples of automatic triggering event include a timer or feedback signals from various sensors. The triggering event can be patient-actuated. One example of a patient-actuated triggering event includes a magnet positioned proximate to the reed switch 737 to toggle the device between or among the different modes. Another example of a patient-actuated triggering event includes a patient-actuated programmer that wirelessly communicates with the device through the transceiver 733 to change modes of operation. In various embodiments, the IMD 701 is adapted to respond to a triggering event by changing therapy modes among a neural stimulation therapy, a CRM therapy, a drug therapy, and various combinations thereof.

One embodiment of the drug delivery device carries the drug between a substructure and an electro-erodible overcoat layer; and another embodiment of the device carries the drug using a drug delivery "chip" that is separately prepared and subsequently attached to the device. The drug is released from the drug delivery chip through an electro-erodible release mechanism. Progressive drug release is provided by wells or regions that are selectively opened by explicitly addressing a given well or region, or by a more generalized progressive erosion of a tapered thickness electro-erodible overcoat layer. The erosion process can be open-loop where a well understood time-erosion behavior is known, or can be closed-loop where the erosion progress is monitored using the known relationship among current, voltage and erosion profile. Either process provides control of the eroded capping layer and consequent drug release.

One embodiment of the drug release chip includes an array of well-like structures constructed so as to laterally isolate one well from another well so that one well is able to be selectively exposed using an electro-erodible process, for example, to deliver a specific drug type and drug dose. An electrically insulating layer covers the well(s) and the surrounding regions. One or more drugs are contained within the well(s). A cap layer of electro-erodible material covers the well(s). The electro-erodible material is non-toxic to the host biosystem both before and after electro-erosion. One example of an electro-erodible material is gold. The connections and cap layer can be patterned to allow individual well caps to be selected for electro-erosion using addressing logic. An electrically insulating, passivation covering insulates all interconnections except the intended electro-erosion region over and perhaps immediately around the drug release well. Alternatively, one or more thickness-graded capping layer(s) are selectively and progressively electro-eroded resulting in controlled progressive exposure of wells in the thinner capped region first. In various embodiments, a current, for a voltage-activated electro-erosion process, or a developed potential, for a current-activated electro-erosion process, are monitored to control the electro-erosion process.

Figure 8:
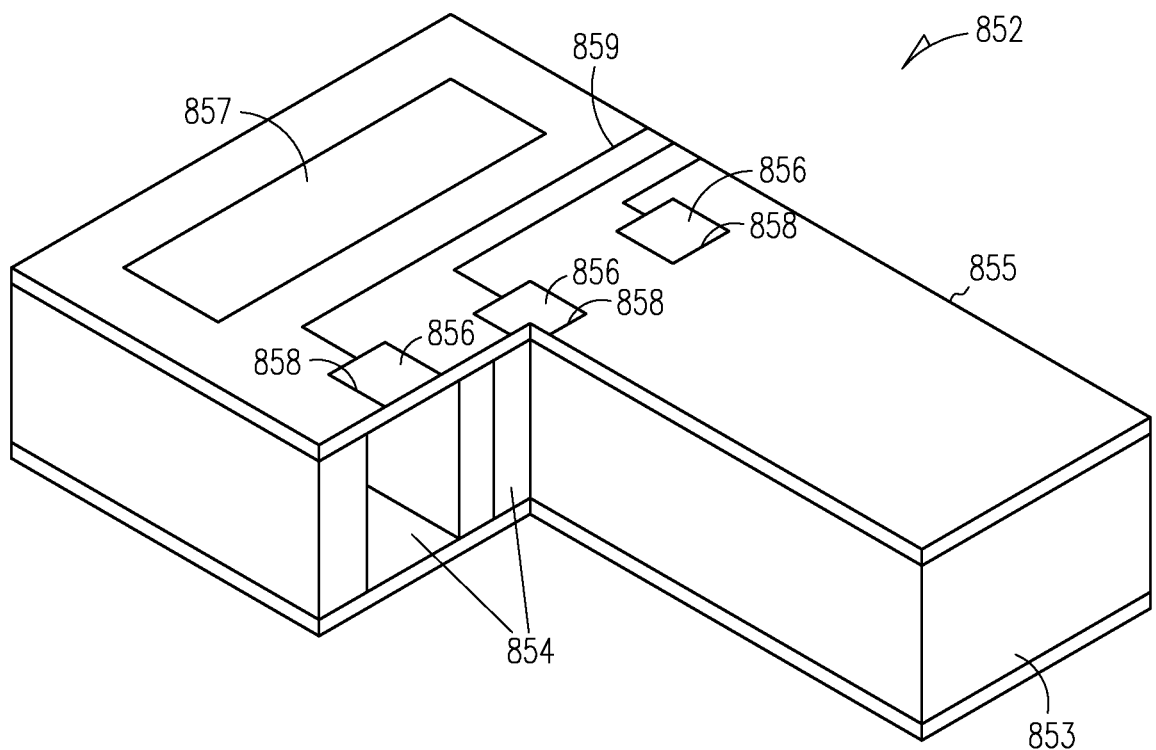
FIG. 8 illustrates one embodiment of a drug delivery microchip for use in one embodiment of a drug-eluting intravascular device.

FIG. 8 illustrates one embodiment of a drug delivery microchip 852 for use in one embodiment of a drug-eluting intravascular device. According to this embodiment, a silicon substrate 853 is formed with voids, wells or micro-reservoirs 854. These micro-reservoirs 854 have a sufficient size, are appropriately lined and are otherwise adapted to store an active substance (e.g. drug) to be released into a biosystem. A coating 855 is formed over the silicon substrate. Electro-erodible caps 856 are formed in the coating over the wells such that, upon being eroded, an opening is formed between the well and the surrounding biosystem. At least one cathode 857 and least one anode 858 are formed in coating 855. According to one embodiment, the at least one anode forms the electro erodible cap 856. Wiring 859 is used to control, or address, the anode to be electro eroded.

Figure 9:
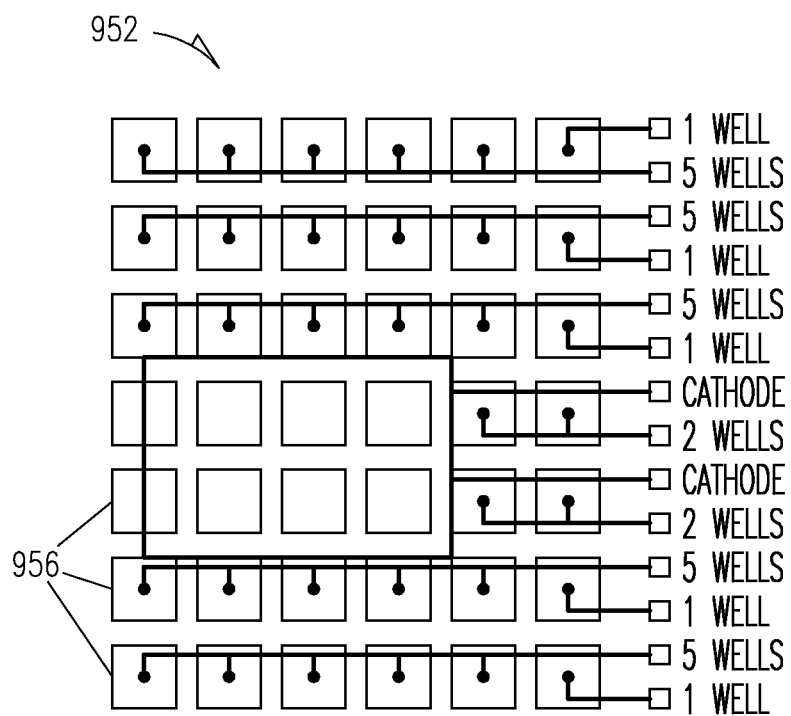
FIG. 9 illustrates one embodiment of a drug delivery microchip capable of delivering different drugs and different dosages of the drugs.

FIG. 9 illustrates one embodiment of a drug delivery microchip 952 capable of delivering different drugs and different dosages of the drugs. The wells within the microchip are addressable; that is, addressable control lines are used to select the wells or well-combinations whose caps 956 are to be electro eroded to elute the active substance contained therein. In the illustrated electrode configuration, there are five sets of one well, five sets of five wells and two sets of two wells. The different sized sets provide different delivery dosages. Alternatively, the physical size of the wells themself are used to control the delivery dosage. Additionally, different drug types are able to be stored in the different sets of wells, such that a desired drug among several is able to be dispensed upon the detection of a particular event.

Figure 10:
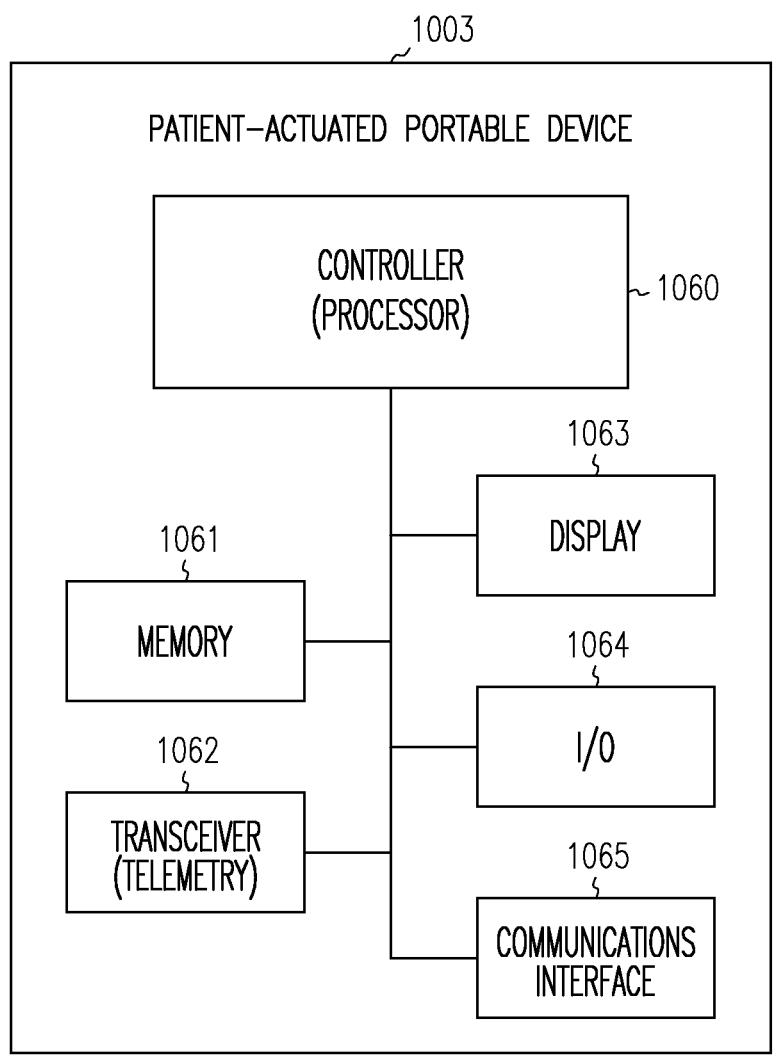
FIG. 10 illustrates a patient-actuated programmer, such as the external patient-actuated device illustrated in the system of FIG. 1, or other external device to communicate with the implantable medical device(s), according to various embodiments of the present subject matter.

FIG. 10 illustrates a patient-actuated programmer 1003, such as the external patient-actuated device 103 illustrated in the system of FIG. 1, or other external device to communicate with the implantable medical device(s), according to various embodiments of the present subject matter. An example of an external device includes Personal Digital Assistants (PDAs) or personal laptop and desktop computers in an Advanced Patient Management (APM) system. The illustrated device includes controller circuitry 1060 and a memory 1061. The controller circuitry is capable of being implemented using hardware, software, and combinations of hardware and software. For example, according to various embodiments, the controller circuitry includes a processor to perform instructions embedded in the memory to perform a number of functions, including communicating data and/or programming instructions to the implantable devices. According to some embodiments, such instructions include instructions for the device to change modes. The illustrated device 1003 further includes a transceiver 1062 and associated circuitry for use to communicate with an implantable device. Various embodiments have wireless communication capabilities. For example, various embodiments of the transceiver and associated circuitry include a telemetry coil for use to wirelessly communicate with an implantable device. The illustrated device 1003 further includes a display 1063, input/output (I/O) devices 1064 such as a display, keyboard, mouse/pointer and/or touch screen, and a communications interface 1065 for use to communicate with other devices, such as over a communication network. The patient-actuated device is able to communicate a trigger command to the IMD to switch to another mode of operation. In an embodiment of the patient-actuated programmer, the instructions contained in memory and operated on by the controller are appropriate to provide a user-friendly interface, with appropriate logical security to prevent inappropriate mode changes, to allow the user to change or otherwise select the modes for the IMD.

Figure 11:
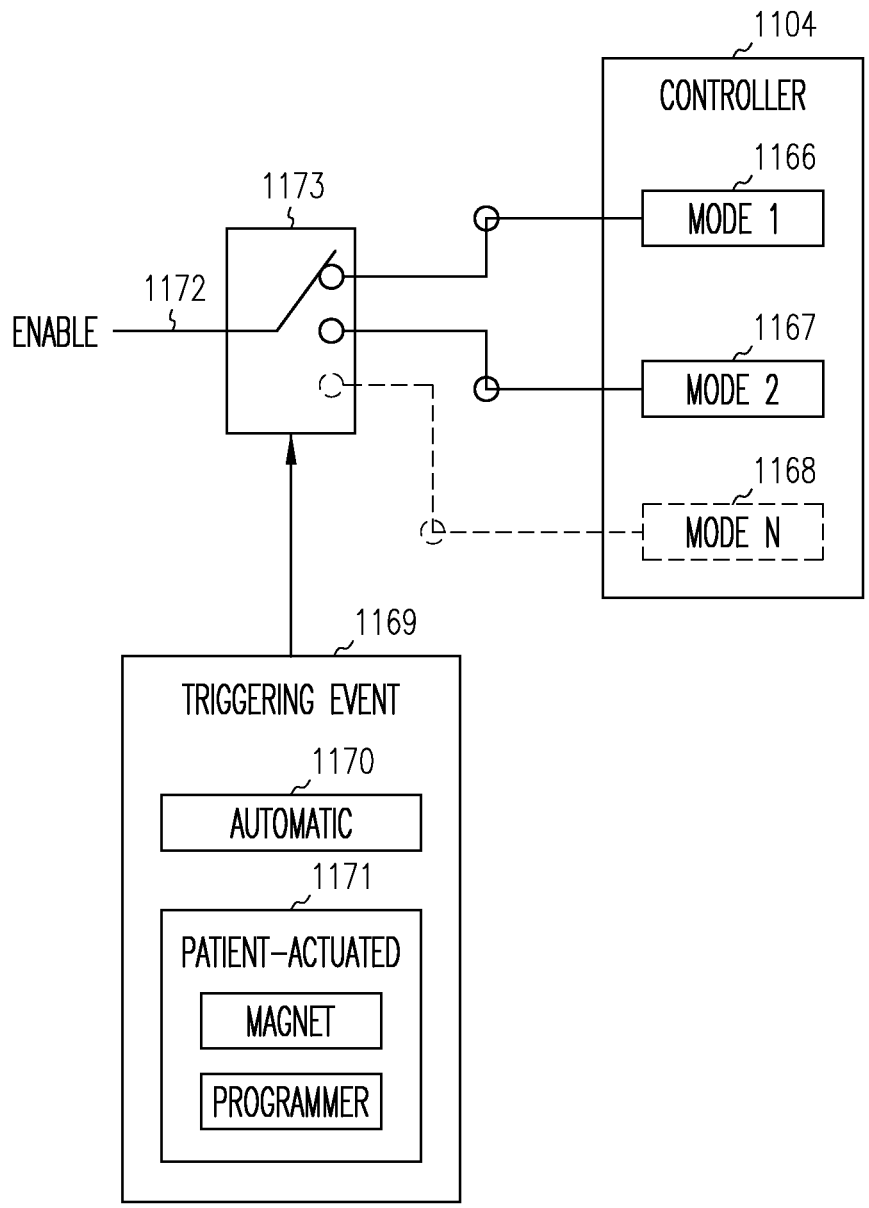
FIG. 11 illustrates an embodiment of a responsive relationship of an IMD controller to a triggering event.

FIG. 11 illustrates an embodiment of a responsive relationship of an IMD controller to a triggering event. The illustration includes a controller 1104 adapted to operate the IMD in a first mode 1166, a second mode 1167 and an Nth mode 1168. The illustration further includes a representation of a triggering event 1169, which can be an automatic event 1170 and/or a patient-actuated event 1171 such as a magnet moved proximate to a reed switch or a patient-actuated programmer. Examples of automatic triggering events include a detected device change such as a detected electrode failure, an End Of Life (EOL) determination for a battery to power the device, a detected lead failure, an environmental change like a detected electrical interference that is capable of interfering with the sensed signal or the application of another therapy capable of interfering with the sensed signal. Automatic triggering events can also include a detected physiologic change such as a detected change in heart rate, a detected arrhythmia, a detected change in a respiratory rate, a detected change in neural traffic, a detected change in blood pressure, and a detected change in activity. Automatic triggering events can also be based on a timer or clock, such as a device with a controller and timer adapted to follow a circadian rhythm when switching modes. The illustration also includes an enable signal 1172 connected to the controller to enable a mode of operation via a switch 1173. The triggering event is adapted to control the switch 1173 to selectively enable a mode of operation by the controller 1104. The illustrated responsive relationship can be performed in hardware, software, or a combination thereof.

Figure 12:
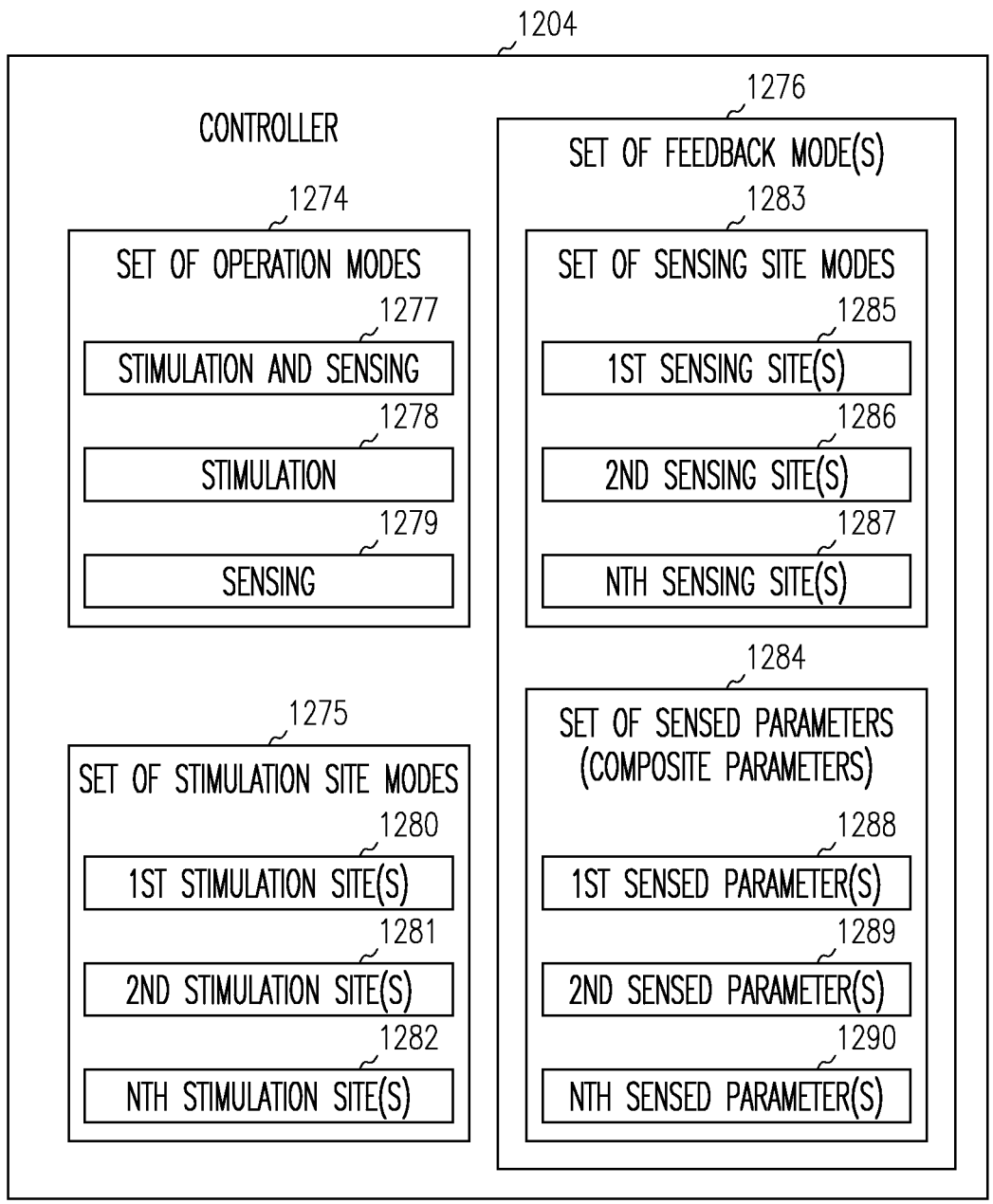
FIG. 12 illustrates an embodiment of a controller capable of switching modes within a set of operation modes, a set of stimulation site modes, and a set of feedback modes.

FIG. 12 illustrates an embodiment of a controller 1204 capable of switching modes within a set of operation modes 1274, a set of stimulation site modes 1275, and a set of feedback modes 1276. With respect to the set of operation modes 1274, the illustrated controller 1204 is adapted to switch between or among two or more modes. An example of an application for switching modes within a set of operation modes 1274 includes switching between therapy and diagnostic modes in response to noise. Examples of modes within the set of operation modes 1274 includes a stimulation and sensing mode 1277 in which closed-loop neural stimulation is provided to neural target(s) based on sensed parameters, a stimulation mode 1278 in which open-loop neural stimulation is provided to neural target(s), and a sensing mode 1279 in which neural stimulation is not provided to neural target(s) but sensing processes continue. Examples of sensed parameters include, but are not limited to, blood pressure, heart rate, and nerve traffic.

With respect to the set of stimulation site modes 1275, the illustrated controller 1204 is adapted to switch between or among two or more stimulation site modes. Examples of applications for switching stimulation site modes 1275 includes switching between parasympathetic and sympathetic nerve stimulation to treat tachycardia-bradycardia syndrome, switching from afferent to efferent stimulation, and changing the dose of the neural stimulation therapy by changing the number of stimulation sites. For example, the illustrated controller is adapted to switch among a mode to stimulate a first stimulation site or sites 1280, a mode to stimulate a second stimulation site or sites 1281, and a mode to stimulate an Nth stimulation site or sites 1282.

With respect to the set of feedback modes 1276, the illustrated controller is adapted to switch among sensing site modes 1283 and to switch among sensed parameter and/or composite parameter modes 1284. Composite parameters are parameters based on two or more other parameters. Examples of applications for switching among sensing site modes 1283 includes recording parasympathetic or sympathetic traffic, recording afferent or efferent traffic, and switching from atrial to ventricular rhythm monitoring. Examples of applications for switching among sensed parameter/composite parameter modes 1284 include detecting short-term brief events such as an impulse burst versus a time-averaged long-term signal trend, and detecting impulse duration versus impulse magnitude. The illustrated controller is adapted to switch among a first site 1285, a second site 1286 and an Nth site 1287 from which to provide sensing for a feedback signal, and is also adapted to switch among a first sensed parameter 1288, a second sensed parameter 1289 and an Nth sensed parameter 1290. Thus, although the sensing site may not change, a different parameter can be detected.

Figure 13:
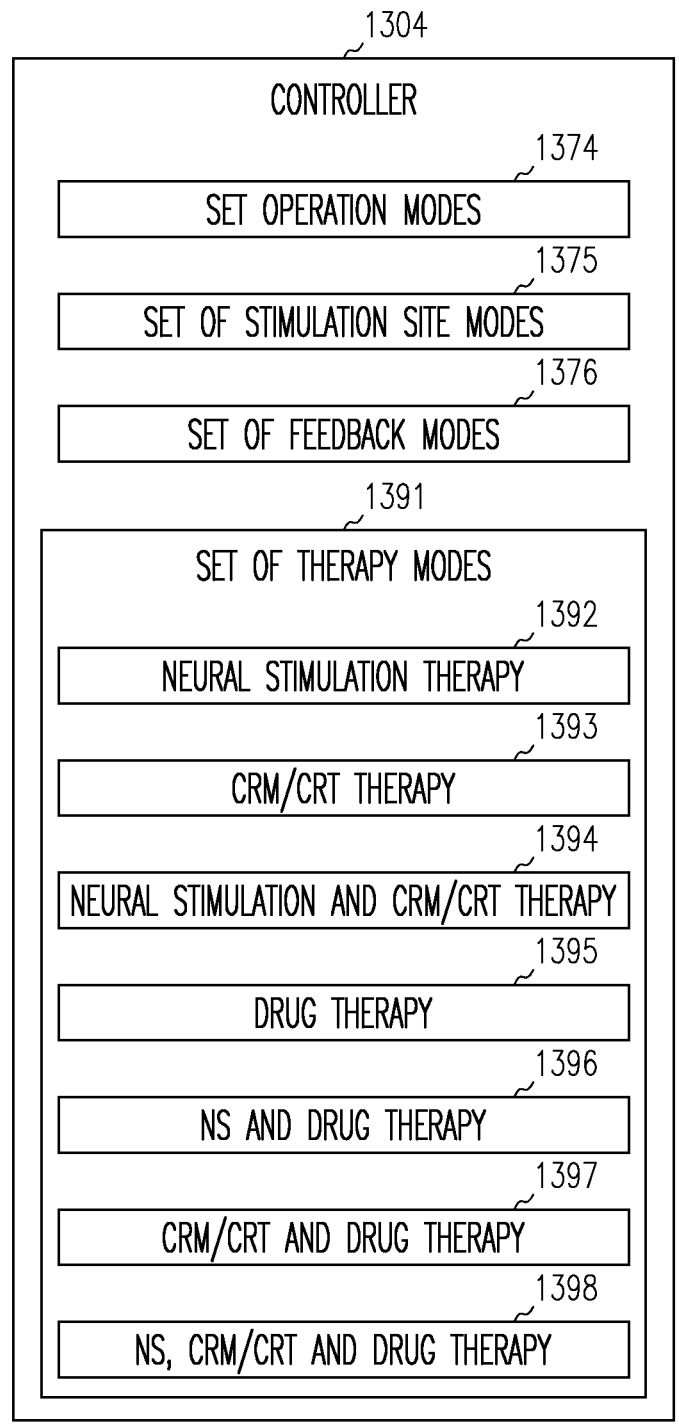
FIG. 13 illustrates an embodiment of a controller capable of switching modes within a set of operation modes, a set of stimulation site modes, a set of feedback modes, and a set of therapy modes.

FIG. 13 illustrates an embodiment of a controller 1304 capable of switching modes within a set of operation modes 1374, a set of stimulation site modes 1375, a set of feedback modes 1376, and a set of therapy modes 1391. Examples of modes 1374, 1375 and 1376 are provided in FIG. 12 at 1274, 1275 and 1276. With respect to the set of therapy modes 1391, the illustrated controller 1304 is adapted to switch between or among two or more modes. Examples of modes within the set of therapy modes includes a neural stimulation therapy mode 1392, a cardiac rhythm management and/or cardiac resynchronization therapy (CRM/CRT) mode 1393, a neural stimulation and CRM therapy mode 1394, a drug therapy mode 1395, a neural stimulation and drug therapy mode 1396, a CRM/CRT and drug therapy mode 1397, and a neural stimulation, CRM/CRT and drug therapy mode 1398. An example of a neural stimulation mode 1392 includes an anti-remodeling, vagal nerve stimulation therapy. An example of a CRM/CRT therapy 1393 includes a resynchronization therapy for a heart failure patient to improve the pumping function of the left ventricle. Examples of a neural stimulation and a CRM/CRT therapy 1394 include a vagal nerve stimulation therapy and anti-tachycardia pacing to terminate arrhythmia, and vagal nerve stimulation in anticipation of a defibrillation shock to reduce the defibrillation threshold. An example of a drug therapy mode 1395 includes an angiogenic growth factor release to treat ischemia. An example of a neural stimulation and a drug therapy mode 1396 includes vagal nerve stimulation and delivery of an angiogenic drug to promote cardiac muscle repair after a myocardial infarction. An example of a CRM/CRT and drug therapy includes pacing to unload a region of a heart damaged by a myocardial infarction such that the damaged heart region works less and delivery of an angiogenic drug to promote cardiac muscle repair. An example of a neural stimulation, CRM/CRM and drug therapy 1398 includes vagal nerve stimulation, pacing to unload a region of a heart damaged by a myocardial infarction, and delivery of an angiogenic drug to prevent post myocardial infarction remodeling.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. With reference to FIG. 5, for example, some embodiments use sensed activity, such as sensed neural activity, in a neural stimulation device to switch modes for a CRM device. The sensed data in the neural stimulation device can be used to alter the mode, rate, AV delay, VV delay, tachyarrhythmia parameters, and various combinations thereof. Some embodiments allow data sensed in a CRM device to mode switch a neural stimulation device.

In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An implantable system, comprising:
   at least one sensor configured to sense a physiologic parameter, the at least one sensor including at least one nerve traffic sensor configured to sense nerve traffic;
   a nerve traffic change detector configured to detect a change in the sensed nerve traffic;
   memory including sets of programmed instructions stored therein to operate the implantable system to provide at least a first sensing mode for nerve traffic sensing and a second sensing mode for nerve traffic sensing and to automatically switch sensing modes in response to a triggering event, wherein the triggering event is determined using the detected change in the sensed nerve traffic; and
   a controller connected to the memory and the at least one sensor, the controller configured to execute the programmed instructions in the memory to operate the implantable system to provide the at least the first sensing mode and the second sensing mode, and to switch the sensing modes in response to the triggering event,
   wherein the implantable system is configured to sense a first physiologic parameter in the first sensing mode and to sense a second physiologic parameter in the second sensing mode, wherein the first and second physiologic parameters are different.

2. The system of claim 1, wherein the implantable system is configured to sense nerve traffic at a first sensing site in the first sensing mode, and sense nerve traffic at a second sensing site in the second sensing mode, wherein the first and second sensing sites are different.

3. The system of claim 1, wherein the implantable system is configured to sense nerve traffic using the at least one nerve traffic sensor in at least one of the first sensing mode or the second sensing mode.

4. The system of claim 1, wherein at least one of the first physiologic parameter or the second physiologic parameter includes a parameter of the sensed nerve traffic.

5. The system of claim 1, wherein the implantable system is configured to sense a first composite physiologic parameter in the first sensing mode and to sensing a second composite physiologic parameter in the second sensing mode.

6. The system of claim 5, wherein at least one of the first composite physiologic parameter or and second composite physiologic parameters is determined using the sensed nerve traffic and at least one other parameter.

7. The system of claim 1, wherein the implantable system is configured to sense a single physiological parameter in one of the first or second sensing modes, and sense a composite physiological parameter in another of the first or second sensing modes, wherein the composite parameter is determined using at least one two sensed physiological parameters.

8. The system of claim 7, wherein at least one of the single physiologic parameter or and composite physiologic parameter is determined using the sensed nerve traffic.

9. The system of claim 1, wherein the implantable system is configured to sense an impulse width of the sensed nerve traffic in one of the first or second sensing modes, and sense an impulse magnitude of the sensed nerve traffic in another of the first or second sensing modes.

10. The system of claim 1, wherein the implantable system is configured to sense a burst of nerve traffic in one of the first or second sensing modes, and sense a trend of the nerve traffic in another of the first or second sensing modes.

11. The system of claim 1, further comprising stimulation circuitry configured to use at least one electrode to provide at least one neural stimulation therapy to at least one neural stimulation target using the at least one electrode.

12. The system of claim 1, wherein the system is configured to use the at least one nerve traffic sensor to sense at least one of: an impulse magnitude, an impulse width, a nerve traffic burst, or a nerve traffic trend.

13. A method implemented using an implantable system that includes at least one nerve traffic sensor, a nerve traffic change detector, a memory, and a control connected to the memory and the at least one sensor, the method including:
sensing nerve traffic using the at least one nerve traffic sensor;
detecting a change in the sensed nerve traffic using the nerve traffic change detector; and
using the controller to execute programmed instructions in the memory to operate the implantable system to provide at least a first sensing mode for nerve traffic sensing and a second sensing mode for nerve traffic sensing, and to switch the sensing modes in response to a triggering event, wherein the triggering event is determined using the detected change in the sensed nerve traffic, wherein a first physiologic parameter is sensed in the first sensing mode and a second physiologic parameter is sensed in the second sensing mode, wherein the first and second physiologic parameters are different.

14. The method of claim 13, wherein the sensing nerve traffic includes sensing nerve traffic at a first sensing site in the first sensing mode, and sensing nerve traffic at a second sensing site in the second sensing mode.

15. The method of claim 13, further comprising sensing nerve traffic using the at least one nerve traffic sensor in at least one of the first sensing mode or the second sensing mode.

16. The method of claim 13, a composite physiologic parameter is sensed in at least one of the first sensing mode and the second sensing mode.

17. A non-transitory machine-readable medium including instructions, which when executed by a machine, cause the machine to:
sense nerve traffic using at least one nerve traffic sensor;
detect a change in the sensed nerve traffic using the nerve traffic change detector; and
provide at least a first sensing mode for nerve traffic sensing and a second sensing mode for nerve traffic sensing, and
switch the sensing modes in response to a triggering event, wherein the triggering event is determined using the detected change in the sensed nerve traffic,
wherein the instructions, which when executed by the machine, cause the machine to sense nerve traffic at a first sensing site in the first sensing mode, and sense nerve traffic at a second sensing site in the second sensing mode, wherein the first and second sensing sites are different.

18. The non-transitory machine-readable medium of claim 17, wherein the instructions, which when executed by the machine, cause the machine to sense an impulse width of the sensed nerve traffic in one of the first or second sensing modes, and sense an impulse magnitude of the sensed nerve traffic in another of the first or second sensing modes.

19. The non-transitory machine-readable medium of claim 17, wherein the instructions, which when executed by the machine, cause the machine to sense a burst of nerve traffic in one of the first or second sensing modes, and sense a trend of the nerve traffic in another of the first or second sensing modes.

20. The non-transitory machine-readable medium of claim 17, wherein a first physiologic parameter is sensed in the first sensing mode and a second physiologic parameter is sensed in the second sensing mode, wherein the first and second physiologic parameters are different.

* * * * *